US009089489B2

(12) United States Patent
Vranderick et al.

(10) Patent No.: US 9,089,489 B2
(45) Date of Patent: Jul. 28, 2015

(54) FORMULATION OF DOXYLAMINE AND PYRIDOXINE AND/OR METABOLITES OR SALTS THEREOF

(71) Applicant: Duchesnay Inc., Blainville, CA (US)

(72) Inventors: Manon Vranderick, St-Lazare, CA (US); Jean-Luc St-Onge, Mirabel, CA (US); Christelle Gedeon, Toronto, CA (US); Michele Gallo, Blainville, CA (US); Éric Gervais, Blainville, CA (US)

(73) Assignee: Duchesnay Inc., Blainville (CA)

( * ) Notice: Subject to any disclaimer, the term of this patent is extended or adjusted under 35 U.S.C. 154(b) by 0 days.

(21) Appl. No.: 14/228,228

(22) Filed: Mar. 27, 2014

(65) Prior Publication Data

US 2014/0314680 A1 Oct. 23, 2014

Related U.S. Application Data

(63) Continuation of application No. PCT/CA2013/050125, filed on Feb. 18, 2013.

(60) Provisional application No. 61/601,754, filed on Feb. 22, 2012.

(51) Int. Cl.
| | |
|---|---|
| *A61K 9/24* | (2006.01) |
| *A61K 31/4402* | (2006.01) |
| *A61K 9/00* | (2006.01) |
| *A61K 31/4415* | (2006.01) |
| *A61K 31/675* | (2006.01) |

(52) U.S. Cl.
CPC ............. *A61K 9/209* (2013.01); *A61K 9/006* (2013.01); *A61K 9/0053* (2013.01); *A61K 31/4402* (2013.01); *A61K 31/4415* (2013.01); *A61K 31/675* (2013.01)

(58) Field of Classification Search
CPC ................................................. A61K 31/4402
USPC ........................................................ 424/468
See application file for complete search history.

(56) References Cited

U.S. PATENT DOCUMENTS

| | | | |
|---|---|---|---|
| 4,842,867 | A | 6/1989 | Ayer et al. |
| 6,197,329 | B1 | 3/2001 | Hermelin et al. |
| 6,340,695 | B1 | 1/2002 | Gervais |
| 6,924,273 | B2 | 8/2005 | Pierce |
| 7,704,542 | B2 | 4/2010 | Bydlon et al. |
| 2007/0141147 | A1 | 6/2007 | Heil et al. |
| 2015/0025032 | A1 | 1/2015 | Vranderick et al. |
| 2015/0025033 | A1 | 1/2015 | Vranderick et al. |

FOREIGN PATENT DOCUMENTS

| | | |
|---|---|---|
| CA | 2 350 195 A1 | 8/2001 |
| JP | 2002-543106 | 12/2002 |
| JP | 2004-521146 | 7/2004 |
| JP | 2008-543723 | 12/2008 |
| WO | WO 03/00263 A1 | 1/2003 |
| WO | WO 2006/017341 A2 | 2/2006 |
| WO | WO 2011/111818 | 9/2011 |
| WO | WO 2011/124953 | 10/2011 |
| WO | WO 2011/163206 | 12/2011 |

OTHER PUBLICATIONS

Gill et al., "Systemic Bioavailability and Pharmacokinetics of the Doxylamine-Pyridoxine Delayed-Release Combination (Diclectin)," *Ther Drug Monit*, 33(1): 115-119 (2011).
Koren et al., "Effectiveness of delayed-release doxylamine and pyridoxine for nausea and vomiting of pregnancy: a randomized placebo controlled trial," *Am J Obstet & Gynecol.*, 203(6): 571.e1-7 (2010).
Nulman et al., "Pharmacokinetic comparison of a delayed-release combination of doxylamine succinate and pyridoxine hydrocholoride (Diclectie®) and oral solutions of these drugs in healthy women of childbearing age," *Can J Clin Pharmacol.*, 16(3): e400-e406 (2009).
Rowland, "Pharmacokinetics of doxylamine given as Bendectine® in the pregnant monkey and baboon," *Reprod Toxicol.*, 3:197-202 (1989).
Slikker, Jr. et al., "Pharmacokinetics of doxylamine, a component of Bendectie®, in the rhesus monkey," *Reprod Toxicol.*, 3: 187-196 (1989).
Notification of Transmittal of the International Search Report and the Written Opinion of the International Searching Authority, or the Declaration, for PCT International Application No. PCT/CA2012/050103, mailed Oct. 18, 2012.

(Continued)

*Primary Examiner* — Jake Vu
(74) *Attorney, Agent, or Firm* — Finnegan, Henderson, Farabow, Garrett & Dunner, LLP

(57) ABSTRACT

A dual release oral dosage system/dosage form comprising an immediate release component/composition and a delayed release component/composition is described. Each of the immediate release component/composition and delayed release component/composition comprises one or more of doxylamine, an analog thereof, a derivative thereof, a prodrug thereof, a metabolite thereof and/or a salt thereof, and one or more of pyridoxine, a salt thereof, a metabolite thereof and/or a salt of the metabolite. The dual release oral dosage system/dosage form exhibits an improved pharmacokinetic profile relative to the current Diclectin® formulation and is useful for example for the alleviation of the symptoms of nausea and vomiting, for example in the case of nausea and vomiting in pregnancy (NVP).

30 Claims, 17 Drawing Sheets

(56) References Cited

OTHER PUBLICATIONS

Notification of Transmittal of the International Search Report and the Written Opinion of the International Searching Authority, or the Declaration, for PCT International Application No. PCT/CA2013/050125, mailed Apr. 25, 2013.

Ashkenazi-Hoffnung et al., "Evaluation of the Efficacy and Safety of Bi-Daily Combination Therapy with Pyridoxine and Doxylamine for Nausea and Vomiting of Pregnancy," *IMAJ*, 15(1): 23-26 (2013).

Notification of Transmittal of the International Search Report and the Written Opinion of the International Searching Authority, or the Declaration, for PCT International Application No. PCT/CA2014/050231, mailed Jun. 5, 2014, (14 pages).

Office Action mailed Jun. 12, 2014, in co-pending U.S. Appl. No. 14/228,214, (9 pages).

Amendment and Response to Restriction Requirement filed Aug. 11, 2014, in co-pending U.S. Appl. No. 14/228,214, (9 pages).

Office Action mailed Sep. 23, 2014, in co-pending U.S. Appl. No. 14/228,214, (19 pages).

U.S. Appl. No. 14/228,214, filed Mar. 27, 2014, Vranderick et al.

U.S. Appl. No. 14/506,387, filed Oct. 3, 2014, Vranderick et al.

Reply to Office Action under 37 C.F.R. § 1.111 filed Dec. 23, 2014, in co-pending U.S. Appl. No. 14/228,214 (19 pages).

Final Office Action mailed Feb. 12, 2015, in co-pending U.S. Appl. No. 14/228,214, (22 pages).

Examination Report for Israeli Patent Application No. 233644 dated Mar. 2, 2015 (including machine translation) (6 pages).

Patent Examination Report No. 1 for Australian Patent Application No. 2013224598 mailed Mar. 5, 2015 (3 pages).

Extended European Search Report for European Patent Application No. 13751706.6 mailed Mar. 31, 2015, (7 pages).

Notice of Reasons for Rejection for Japanese Patent Application No. 2014-557951 dated Mar. 27, 2015, (6 pages).

|  |  | Fasted in women | Fed in women | delta | Single dose in women | Multi dose in women | delta |
|---|---|---|---|---|---|---|---|
| Pyridoxine | | | | | | | |
| | AUC inf ng/mL | 40 | 24 | -40% | 43 | 64ʳ | +50% |
| | Cmax ng/mL | 35 | 14 | -60% | 33 | 46ʳ | +40% |
| | Tmax hr | 2.5 | 9.25 | +7h | 5.5 | 5.5 | = |
| | T1/2 hr | 0.4 | 0.5 | = | 0.5 | 0.5 | = |
| Pyridoxal | | | | | | | |
| | AUC inf ng/mL | 231 | 197 | -15% | 211 | 1587ʳ | +650% |
| | Cmax ng/mL | 85 | 46 | -45% | 74 | 210ʳ | +184% |
| | Tmax hr | 3 | 10 | +7h | 6 | 6.8 | = |
| | T1/2 hr | 2 | 2 | = | 1.3 | 19 | +18h |
| PLP | | | | | | | |
| | AUC inf ng/mL | 2415 | 2839ʳ | +17% | 1536 | 6100ʳ | +297% |
| | Cmax ng/mL | 30 | 34 | = | 30 | 85ʳ | +183% |
| | Tmax hr | 12 | 16 | +4h | 11.5 | 6 | -5h |
| | T1/2 hr | 82 | 95ʳ | +15% | 37 | 54 | 45% |
| Doxy | | | | | | | |
| | AUC inf ng/mL | 1448 | 1579 | = | 1281 | 3721ʳ | +190% |
| | Cmax ng/mL | 94.9 | 75.74 | -20% | 83.3 | 168.6ʳ | +104% |
| | Tmax hr | 5 | 12 | +7h | 7.2 | 7.8 | = |
| | T1/2 hr | 12.64 | 12.48 | = | 10.1 | 11.9 | = |

FIG. 2

Diclectin® Fed Conditions (B) vs Diclectin® Fasting Conditions (A)

| Doxylamine | AUC$_{0-t}$ | AUC$_{0-inf}$* | C$_{max}$ |
|---|---|---|---|
| Ratio[1] | 102.86% | 108.81% | 79.61% |
| 90 % Geometric C.I.[2] | 96.92 % to 109.15 % | 104.33 % to 113.49 % | 74.73 % to 84.81 % |
| Intra-Subject CV | 16.24 % | 10.57 % | 17.31 % |

[1] Calculated using least-squares means according to the formula: $e^{(Diclectin® Fed Conditions (B) - Diclectin® Fasting Conditions (A))} \times 100$
[2] 90% Geometric Confidence Interval using ln-transformed data
* For this parameter, N = 37.

FIG. 3A

| Diclectin® Fed Conditions (B) vs Diclectin® Fasting Conditions (A) ||||
|---|---|---|---|
| Pyridoxine | $AUC_{0-t}$ <br> N = 33 | $AUC_{0-inf}$ <br> N = 12 | $C_{max}$ <br> N = 33 |
| Ratio[1] | 44.62% | 61.45% | 32.39% |
| 90 % Geometric C.I.[2] | 31.26 % to 63.68 % | 40.31 % to 93.67 % | 22.79 % to 46.03 % |
| Intra-Subject CV | 102.22 % | 58.03 % | 100.52 % |

[1] Calculated using least-squares means according to the formula: $e^{(Diclectin® Fed Conditions (B) - Diclectin® Fasting Conditions (A))}$ X 100
[2] 90% Geometric Confidence Interval using ln-transformed data

FIG. 3B

| | $AUC_{0-24\ (ng/mL)}$ after 20 mg day 1 | $AUC_{0-24\ (ng/mL)}$ after 20 mg day 18 | Accumulation index AI $AUC_{0-24}$ day 18 / $AUC_{0-24}$ day 1 |
|---|---|---|---|
| Doxy | 911.4 | 2531.5 | 2.76 |
| PYR | 40.7 | 62.7 | 1.59 |
| PYL | 195.1 | 1147.2 | 3.09 |
| PLP | 442 | 1725 | 3.98 |
| PYM | 0.57 | 1.79 | 3.16 |
| PMP | 3.504 | 17.08 | 4.88 |

FIG. 4

Doxylamine

| subject | dose | treatment | AUCt (ng/mL) | AUCt intra study %cv | Cmax (ng/mL) | Cmax intra study %cv | Tmax (hr) | Tmax intra study %cv | T1/2 (hr) | T1/2 intra study %cv |
|---|---|---|---|---|---|---|---|---|---|---|
| 18 women | 20mg | fasted | 1678.19 | 32.7 | 90.4 | 14.5 | 6.1 | 29.0 | 11.8 | 28.9 |
| 24 women | 20mg | fasted | 1519.79 | 8.5 | 85.9 | 20.6 | 5.3 | 29.5 | 11.7 | 19.9 |
| 42 women | 20mg | fasted | 1407.20 | 23.9 | 94.9 | 19.4 | 5.1 | 66.1 | 12.6 | 27.2 |
| 18 women | 20mg | fasted | 911.40 | 22.6 | 83.3 | 24.8 | 7.2 | 25.9 | 10.1 | 20.8 |
| 24 women | 20mg | fed | 1567.23 | 23.4 | 82.0 | 18.9 | 10.6 | 17.0 | 12.0 | 15.9 |
| 42 women | 20mg | fed | 1488.03 | 31.1 | 75.7 | 21.9 | 14.9 | 49.2 | 12.5 | 23.1 |
| 18 women | 40mg | multidose | 3661.27 | 34.9 | 168.6 | 22.8 | 7.8 | 20.7 | 11.9 | 28.0 |
| | | average %CV | | 25.3 | | 20.4 | | 33.9 | | 23.4 |

Pyridoxine

| subject | dose | treatment | AUCt (ng/mL) | AUCt intra study %cv | Cmax (ng/mL) | Cmax intra study %cv | Tmax (hr) | Tmax intra study %cv | T1/2 (hr) | T1/2 intra study %cv |
|---|---|---|---|---|---|---|---|---|---|---|
| 18 women | 20mg | fasted | 39.34 | 42.0 | 32.4 | 46.1 | 5.7 | 26.7 | 0.5 | 47.4 |
| 24 women | 20mg | fasted | 33.75 | 40.6 | 35.5 | 61.0 | 2.5 | 37.7 | 0.4 | 42.3 |
| 42 women | 20mg | fasted | | | 55.1 | 36.8 | 2.7 | 40.2 | | |
| 18 women | 20mg | fasted | 51.41 | 45.2 | 50.7 | 61.1 | 3.8 | 31.4 | 0.3 | 44.5 |
| 24 women | 20mg | fed | | | 24.0 | 58.3 | 7.7 | 22.5 | | |
| 42 women | 20mg | fed | | | | | | | | |
| 18 women | 40mg | multidose | 59.53 | 57.2 | 46.1 | 61.5 | 5.6 | 22.2 | 0.5 | 30.0 |
| | | average %CV | | 46.2 | | 54.1 | | 30.1 | | 41.1 |

FIG. 5

FORMULATION OF DOXYLAMINE AND PYRIDOXINE AND/OR METABOLITES OR SALTS THEREOF

CROSS REFERENCE TO RELATED APPLICATIONS

This application is a Continuation application of PCT application no. PCT/CA2013/050125 filed on Feb. 18, 2013 and published in English under PCT Article 21(2), which itself claims the benefit of U.S. provisional application Ser. No. 61/601,754, filed on Feb. 22, 2012. All documents above are incorporated herein in their entirety by reference.

FIELD OF THE INVENTION

The present invention generally relates to dosage systems and forms and uses and kits thereof, for example for the management of nausea and vomiting, such as for the prevention and/or treatment of nausea and vomiting in pregnancy (NVP).

BACKGROUND OF THE INVENTION

Nausea and vomiting of pregnancy (NVP), also referred to as "morning sickness," is very common. It afflicts 50% to 80% of pregnant women with varying degrees of severity.

Commonly occurring within the first 4 to 16 weeks of pregnancy, approximately 20% of women will continue to experience NVP for a longer period of time. Some women may suffer from NVP until the end of the pregnancy. Nausea and vomiting can have serious adverse effects. If severe enough, NVP can cause dehydration, with associated salt and vitamin imbalances. These and other effects can be harmful to the health of the woman and the well-being of her baby. In its most severe form, NVP may manifest itself as hyperemesis gravidarum, a potentially life threatening condition affecting 0.5% to 2% of pregnancies, which is characterized by protracted vomiting, retching, severe dehydration, and weight loss requiring hospitalization.

The delayed release combination of Doxylamine succinate/pyridoxine HCl (10 mg each), marketed in Canada under the trade-name Diclectin®, is the only medication approved in Canada for the treatment of NVP. Its safety and effectiveness for the treatment of NVP is recognized by the medical community, and its safety throughout pregnancy has been long established.

Nevertheless, there is a need for the development of novel pharmaceutical dosage systems and forms, for example those having an improved pharmacokinetics profile, for the prevention and treatment of nausea and vomiting, such as in NVP.

The present description refers to a number of documents, the content of which is herein incorporated by reference in their entirety.

SUMMARY OF THE INVENTION

The present invention relates to pharmaceutical compositions and dosage systems, as well as related methods, uses and kits. The pharmaceutical compositions, dosage systems methods, uses and kits may be used for example for the management of nausea and vomiting, such as for the prevention and/or treatment of nausea and vomiting of pregnancy (NVP).

The present invention generally relates to dosage systems and forms and uses and kits thereof.

In a first aspect, the present invention provides a dual release oral dosage system comprising (a) a doxylamine component, i.e. one or more of (i) doxylamine, (ii) an analog thereof, (iii) a derivative thereof, (iv) a prodrug thereof, (v) a metabolite thereof and (vi) a salt of any of (i)-(v); and (b) a pyridoxine component, i.e. one or more of (i) pyridoxine, (ii) an analog thereof, (iii) a derivative thereof, (iv) a prodrug thereof, (v) a metabolite thereof and (vi) a salt of any of (i)-(v), said dual release oral dosage system comprising:

(A) an immediate release component comprising: (a) one or more of (i) doxylamine, (ii) an analog thereof, (iii) a derivative thereof, (iv) a prodrug thereof, (v) a metabolite thereof and (vi) a salt of any of (i)-(v); and/or (b) one or more of (i) pyridoxine, (ii) an analog thereof, (iii) a derivative thereof, (iv) a prodrug thereof, (v) a metabolite thereof and (vi) a salt of any of (i)-(v); and (B) a delayed release component comprising: (a) one or more of (i) doxylamine, (ii) an analog thereof, (iii) a derivative thereof, (iv) a prodrug thereof, (v) a metabolite thereof and/or (vi) a salt of any of (i)-(v); and/or (b) one or more of (i) pyridoxine, (ii) an analog thereof, (iii) a derivative thereof, (iv) a prodrug thereof, (v) a metabolite thereof and (vi) a salt of any of (i)-(v);

wherein the immediate release component is for effecting release of (a) one or more of (i) doxylamine, (ii) an analog thereof, (iii) a derivative thereof, (iv) a prodrug thereof, (v) a metabolite thereof and/or (vi) a salt of any of (i)-(v), and/or (b) (i) one or more of (i) pyridoxine, (ii) an analog thereof, (iii) a derivative thereof, (iv) a prodrug thereof, (v) a metabolite thereof and (vi) a salt of any of (i)-(v), which begins prior to release of (a) one or more of (i) doxylamine, (ii) an analog thereof, (iii) a derivative thereof, (iv) a prodrug thereof, (v) a metabolite thereof and/or (vi) a salt of any of (i)-(v), and/or (b) (i) one or more of (i) pyridoxine, (ii) an analog thereof, (iii) a derivative thereof, (iv) a prodrug thereof, (v) a metabolite thereof and (vi) a salt of any of (i)-(v), from the delayed release component, within the gastrointestinal tract.

In an embodiment, the above-mentioned immediate release component is for effecting release substantially within the stomach.

In an embodiment, the above-mentioned delayed release component is for effecting release substantially within the intestine and there is substantially no release from the delayed release composition in the stomach.

In an embodiment, the above-mentioned system provides a maximum daily dosage of (i) doxylamine (ii) an analog thereof, (iii) a derivative thereof, (iv) a prodrug thereof, (v) a metabolite thereof and/or (vi) a salt of any of (i)-(v), of about 60 mg. In a further embodiment, the above-mentioned system provides a daily dosage of (i) doxylamine (ii) an analog thereof, (iii) a derivative thereof, (iv) a prodrug thereof, (v) a metabolite thereof and/or (vi) a salt of any of (i)-(v), of about 20 mg to about 60 mg.

In an embodiment, the above-mentioned system provides an average $C_{max}$ of doxylamine (ii) an analog thereof, (iii) a derivative thereof, (iv) a prodrug thereof, (v) a metabolite thereof and/or (vi) a salt of any of (i)-(v), up to about 250 ng/ml. In a further embodiment, the above-mentioned system provides an average $C_{max}$ of doxylamine (ii) an analog thereof, (iii) a derivative thereof, (iv) a prodrug thereof, (v) a metabolite thereof and/or (vi) a salt of any of (i)-(v), of about 70 ng/ml to about 250 ng/ml.

In an embodiment, the above-mentioned system provides a maximum daily dosage of (i) pyridoxine (ii) an analog thereof, (iii) a derivative thereof, (iv) a prodrug thereof, (v) a metabolite thereof and/or (vi) a salt of any of (i)-(v), of about 100 mg.

In an embodiment, the above-mentioned system provides a daily dosage of (i) pyridoxine and (ii) an analog thereof, (iii) a derivative thereof, (iv) a prodrug thereof, (v) a metabolite thereof and/or (vi) a salt of any of (i)-(v); of about 1 mg to about 100 mg.

In an embodiment, the above-mentioned system provides an average $C_{max}$ of (i) pyridoxine and/or a pharmaceutically acceptable salt thereof, (ii) a metabolite of pyridoxine and/or a pharmaceutically acceptable salt of the metabolite, or (iii) both (i) and (ii), of up to about 300 ng/ml. In a further embodiment, the above-mentioned system provides an average $C_{max}$ of (i) pyridoxine (ii) an analog thereof, (iii) a derivative thereof, (iv) a prodrug thereof, (v) a metabolite thereof and/or (vi) a salt of any of (i)-(v); of about 10 ng/ml to about 300 ng/ml.

In an embodiment, the above-mentioned system comprises at least two dual release oral dosage forms, wherein each of the oral dosage forms comprises:

(A) an immediate release composition comprising: (a) one or more of (i) doxylamine, (ii) an analog thereof, (iii) a derivative thereof, (iv) a prodrug thereof, (v) a metabolite thereof and (vi) a salt of any of (i)-(v); and/or (b) one or more of (i) pyridoxine, (ii) an analog thereof, (iii) a derivative thereof, (iv) a prodrug thereof, (v) a metabolite thereof and (vi) a salt of any of (i)-(v); and (B) a delayed release composition comprising: (a) one or more of (i) doxylamine, (ii) an analog thereof, (iii) a derivative thereof, (iv) a prodrug thereof, (v) a metabolite thereof and/or (vi) a salt of any of (i)-(v); and/or (b) one or more of (i) pyridoxine, (ii) an analog thereof, (iii) a derivative thereof, (iv) a prodrug thereof, (v) a metabolite thereof and (vi) a salt of any of (i)-(v).

In an embodiment, the above-mentioned system consists of two to four of the dual release oral dosage forms. In a further embodiment, the above-mentioned system consists of two of the dual release oral dosage forms.

In an embodiment, at least two of the above-mentioned dual release oral dosage forms are the same. In another embodiment, all of the above-mentioned dual release oral dosage forms are the same.

In an embodiment, at least two of the above-mentioned dual release oral dosage forms are different. In another embodiment, all of the above-mentioned dual release oral dosage forms are different.

In an embodiment, each of the above-mentioned different dual release oral dosage forms comprises an identifying characteristic such that the different dual release oral dosage forms can be distinguished from one another. In a further embodiment, the above-mentioned identifying characteristic is shape, color, an identifying mark, or any combination thereof.

In an embodiment, the above-mentioned immediate release composition and delayed release composition are comprised in the dual release oral dosage form in a layered arrangement with respect to one another.

In another embodiment, the above-mentioned immediate release composition and delayed release composition are comprised in the dual release oral dosage form adjacent to one another.

In an embodiment, the above-mentioned dual release oral dosage form comprises (a) a core comprising the delayed release composition and (b) one or more coats substantially surrounding the core, the one or more coats comprising the immediate release composition.

In an embodiment, the above-mentioned dual release oral dosage form comprises (a) delayed release granules or microspheres comprising the delayed release composition and (b) immediate release granules or microspheres comprising the immediate release composition.

In an embodiment, the above-mentioned immediate release composition is in contact with the delayed release composition, within the dual release oral dosage form.

In another embodiment, the above-mentioned immediate release composition is not in contact with the delayed release composition, within the dual release oral dosage form.

In an embodiment, the above-mentioned immediate release composition, delayed release composition, or both, further comprise at least one pharmaceutically acceptable carrier or excipient (e.g., at least one carrier or excipient acceptable for administration to a pregnant female).

In an embodiment, the above-mentioned immediate release component or composition comprises (a) doxylamine and/or a pharmaceutically acceptable salt thereof; and/or (b) (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned metabolite is pyridoxal, pyridoxal-5-phosphate, pyridoxamine, pyridoxamine-5-phosphate or pyridoxine phosphate.

In an embodiment, the above-mentioned immediate release component or composition comprises (a) doxylamine and/or a pharmaceutically acceptable salt thereof; and/or (b) (i) pyridoxine (ii) an analog thereof, (iii) a derivative thereof, (iv) a prodrug thereof, (v) a metabolite or two or more metabolites thereof, and/or (vi) a salt of any of (i)-(v).

In an embodiment, the above-mentioned delayed release component or composition comprises (a) doxylamine and/or a pharmaceutically acceptable salt thereof; and/or (b) (i) pyridoxine (ii) an analog thereof, (iii) a derivative thereof, (iv) a prodrug thereof, (v) a metabolite thereof and/or (vi) a salt of any of (i)-(v);

In an embodiment, the above-mentioned delayed release component or composition comprises (a) doxylamine and/or a pharmaceutically acceptable salt thereof; and/or (b) (i) pyridoxine (ii) an analog thereof, (iii) a derivative thereof, (iv) a prodrug thereof, (v) a metabolite or two or more metabolites thereof, and/or (vi) a salt of any of (i)-(v).

In a further embodiment, the above-mentioned two or more metabolites are any combination of two or more of pyridoxal, pyridoxal-5-phosphate, pyridoxamine, pyridoxamine-5-phosphate and pyridoxine phosphate.

In an embodiment, the above-mentioned dual release oral dosage form is a tablet, pill, capsule, solution or flowable powder.

In another aspect, the present invention provides a dual release oral dosage form comprising (a) a doxylamine component, i.e. one or more of (i) doxylamine, (ii) an analog thereof, (iii) a derivative thereof, (iv) a prodrug thereof, (v) a metabolite thereof and (vi) a salt of any of (i)-(v); and (b) a pyridoxine component, i.e. one or more of (i) pyridoxine, (ii) an analog thereof, (iii) a derivative thereof, (iv) a prodrug thereof, (v) a metabolite thereof and (vi) a salt of any of (i)-(v), said dual release oral dosage form comprising:

(A) an immediate release composition comprising: (a) one or more of (i) doxylamine, (ii) an analog thereof, (iii) a derivative thereof, (iv) a prodrug thereof, (v) a metabolite thereof and (vi) a salt of any of (i)-(v); and/or (b) one or more of (i) pyridoxine, (ii) an analog thereof, (iii) a derivative thereof, (iv) a prodrug thereof, (v) a metabolite thereof and (vi) a salt of any of (i)-(v); and (B) a delayed release composition comprising: (a) one or more of (i) doxylamine, (ii) an analog thereof, (iii) a derivative thereof, (iv) a prodrug thereof, (v) a metabolite thereof and (vi) a salt of any of (i)-(v); and/or (b) one or more of (i)

pyridoxine, (ii) an analog thereof, (iii) a derivative thereof, (iv) a prodrug thereof, (v) a metabolite thereof and (vi) a salt of any of (i)-(v);

wherein the immediate release composition is for effecting release of (a) one or more of (i) doxylamine, (ii) an analog thereof, (iii) a derivative thereof, (iv) a prodrug thereof, (v) a metabolite thereof and/or (vi) a salt of any of (i)-(v), and/or (b) (i) one or more of (i) pyridoxine, (ii) an analog thereof, (iii) a derivative thereof, (iv) a prodrug thereof, (v) a metabolite thereof and (vi) a salt of any of (i)-(v), which begins prior to release of (a) one or more of (i) doxylamine, (ii) an analog thereof, (iii) a derivative thereof, (iv) a prodrug thereof, (v) a metabolite thereof and/or (vi) a salt of any of (i)-(v), and/or (b) (i) one or more of (i) pyridoxine, (ii) an analog thereof, (iii) a derivative thereof, (iv) a prodrug thereof, (v) a metabolite thereof and (vi) a salt of any of (i)-(v), from the delayed release component, within the gastrointestinal tract.

In an embodiment, the above-mentioned immediate release composition is for effecting release substantially within the stomach.

In an embodiment, the above-mentioned delayed release composition is for effecting release substantially within the intestine, and there is substantially no release from the delayed release composition in the stomach.

In an embodiment, the above-mentioned dosage form comprises about 40 mg or less of (i) doxylamine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises about 30 mg or less of (i) doxylamine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises about 20 mg or less of (i) doxylamine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises about 10 mg or less of (i) doxylamine (ii) an analog thereof, (iii) a derivative thereof, (iv) a prodrug thereof, (v) a metabolite thereof and/or (vi) a salt of any of (i)-(v).

In an embodiment, the above-mentioned dosage form comprises at least about 5 mg of (i) doxylamine (ii) an analog thereof, (iii) a derivative thereof, (iv) a prodrug thereof, (v) a metabolite thereof and/or (vi) a salt of any of (i)-(v).

In an embodiment, the above-mentioned dosage form comprises from about 5 mg to about 40 mg of (i) doxylamine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises from about 5 mg to about 30 mg of (i) doxylamine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises from about 5 mg to about 20 mg of (i) doxylamine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises from about 5 mg to about 10 mg of (i) doxylamine (ii) an analog thereof, (iii) a derivative thereof, (iv) a prodrug thereof, (v) a metabolite thereof and/or (vi) a salt of any of (i)-(v).

In an embodiment, the above-mentioned dosage form comprises from about 10 mg to about 20 mg of (i) doxylamine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises about 20 mg of (i) doxylamine (ii) an analog thereof, (iii) a derivative thereof, (iv) a prodrug thereof, (v) a metabolite thereof and/or (vi) a salt of any of (i)-(v).

In an embodiment, the above-mentioned dosage form comprises about 80 mg or less of (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises about 50 mg or less of (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises about 25 mg or less of (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises about 20 mg or less of (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises about 10 mg or less of (i) pyridoxine (ii) an analog thereof, (iii) a derivative thereof, (iv) a prodrug thereof, (v) a metabolite thereof and/or (vi) a salt of any of (i)-(v).

In an embodiment, the above-mentioned dosage form comprises at least about 5 mg of (I) pyridoxine (ii) an analog thereof, (iii) a derivative thereof, (iv) a prodrug thereof, (v) a metabolite thereof and/or (vi) a salt of any of (i)-(v).

In an embodiment, the above-mentioned dosage form comprises from about 5 mg to about 80 mg of (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises from about 5 mg to about 50 mg of (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises from about 5 mg to about 25 mg of (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises from about 10 mg to about 25 mg of (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises from about 10 mg to about 20 mg of (i) pyridoxine (ii) an analog thereof, (iii) a derivative thereof, (iv) a prodrug thereof, (v) a metabolite thereof and/or (vi) a salt of any of (i)-(v). In a further embodiment, the above-mentioned dosage form comprises about 20 mg of (i) pyridoxine (ii) an analog thereof, (iii) a derivative thereof, (iv) a prodrug thereof, (v) a metabolite thereof and/or (vi) a salt of any of (i)-(v).

In an embodiment, the above-mentioned dosage form comprises an identifying characteristic for correlation with its administration in a dosage regimen. In a further embodiment, the above-mentioned identifying characteristic is shape, color, an identifying mark, or any combination thereof.

In an embodiment, the above-mentioned immediate release composition and the delayed release composition are comprised in the dual release oral dosage form in a layered arrangement with respect to one another.

In another embodiment, the above-mentioned immediate release composition and the delayed release composition are comprised in the dual release oral dosage form adjacent to one another.

In an embodiment, the above-mentioned dual release oral dosage form comprises (a) a core comprising the delayed release composition and (b) one or more coats substantially surrounding the core, the one or more coats comprising the immediate release composition.

In an embodiment, the above-mentioned dual release oral dosage form comprises (a) delayed release granules or microspheres comprising the delayed release composition and (b) immediate release granules or microspheres comprising the immediate release composition.

In an embodiment, the above-mentioned immediate release composition is in contact with the delayed release composition, within the dual release oral dosage form.

In another embodiment, the above-mentioned immediate release composition is not in contact with the delayed release composition, within the dual release oral dosage form.

In an embodiment, the above-mentioned immediate release composition, delayed release composition, or both, further comprise at least one pharmaceutically acceptable carrier or excipient.

In an embodiment, the above-mentioned immediate release composition comprises (a) (i) doxylamine (ii) an analog thereof, (iii) a derivative thereof, (iv) a prodrug thereof, (v) a metabolite thereof and/or (vi) a salt of any of (i)-(v); and/or (b) (i) pyridoxine (ii) an analog thereof, (iii) a derivative thereof, (iv) a prodrug thereof, (v) a metabolite thereof and/or (vi) a salt of any of (i)-(v).

In an embodiment, the above-mentioned immediate release composition comprises (a) (i) doxylamine (ii) an analog thereof, (iii) a derivative thereof, (iv) a prodrug thereof, (v) a metabolite thereof and/or (vi) a salt of any of (i)-(v); and/or (b) (i) pyridoxine (ii) an analog thereof, (iii) a derivative thereof, (iv) a prodrug thereof, (v) a metabolite or two or more metabolites thereof, and/or (vi) a salt of any of (i)-(v).

In an embodiment, the above-mentioned delayed release component or composition comprises (a) doxylamine and/or a pharmaceutically acceptable salt thereof; and/or (b) (i) pyridoxine (ii) an analog thereof, (iii) a derivative thereof, (iv) a prodrug thereof, (v) a metabolite thereof and (vi) a salt of any of (i)-(v).

In an embodiment, the above-mentioned delayed release component or composition comprises (a) doxylamine and/or a pharmaceutically acceptable salt thereof; and/or (b) (i) pyridoxine (ii) an analog thereof, (iii) a derivative thereof, (iv) a prodrug thereof, (v) a metabolite or two or more metabolites thereof, and/or (vi) a salt of any of (i)-(v).

In a further embodiment, the above-mentioned metabolite is pyridoxal, pyridoxal-5-phosphate, pyridoxamine, pyridoxamine-5-phosphate or pyridoxine phosphate.

In a further embodiment, the above-mentioned two or more metabolites are any combination of two or more of pyridoxal, pyridoxal-5-phosphate, pyridoxamine, pyridoxamine-5-phosphate and pyridoxine phosphate.

In an embodiment, the above-mentioned dual release oral dosage form is a tablet, pill, capsule, solution or flowable powder.

In an embodiment, the amount of (i) doxylamine, (ii) an analog thereof, (iii) a derivative thereof, (iv) a prodrug thereof, (v) a metabolite thereof and/or (vi) a salt of any of (i)-(v), comprised in the immediate release component or composition is less than the amount of doxylamine (ii) an analog thereof, (iii) a derivative thereof, (iv) a prodrug thereof, (v) a metabolite thereof and/or (vi) a salt of any of (i)-(v), comprised in the delayed release component or composition.

In another embodiment, the amount of (i) doxylamine (ii) an analog thereof, (iii) a derivative thereof, (iv) a prodrug thereof, (v) a metabolite thereof and/or (vi) a salt of any of (i)-(v), comprised in the immediate release component or composition is more than the amount of (i) doxylamine (ii) an analog thereof, (iii) a derivative thereof, (iv) a prodrug thereof, (v) a metabolite thereof and/or (vi) a salt of any of (i)-(v), comprised in the delayed release component or composition.

In another embodiment, the amount of (i) doxylamine (ii) an analog thereof, (iii) a derivative thereof, (iv) a prodrug thereof, (v) a metabolite thereof and/or (vi) a salt of any of (i)-(v), comprised in the immediate release component or composition is substantially equivalent to the amount of doxylamine (ii) an analog thereof, (iii) a derivative thereof, (iv) a prodrug thereof, (v) a metabolite thereof and/or (vi) a salt of any of (i)-(v), comprised in the delayed release component or composition.

In an embodiment, the amount of (i) pyridoxine (ii) an analog thereof, (iii) a derivative thereof, (iv) a prodrug thereof, (v) a metabolite thereof and/or (vi) a salt of any of (i)-(v); comprised in the immediate release component or composition is less than the amount of (i) pyridoxine (ii) an analog thereof, (iii) a derivative thereof, (iv) a prodrug thereof, (v) a metabolite thereof and/or (vi) a salt of any of (i)-(v); comprised in the delayed release component or composition.

In another embodiment, the amount of (i) pyridoxine (ii) an analog thereof, (iii) a derivative thereof, (iv) a prodrug thereof, (v) a metabolite thereof and/or (vi) a salt of any of (i)-(v), comprised in the immediate release component or composition is more than the amount of (i) pyridoxine (ii) an analog thereof, (iii) a derivative thereof, (iv) a prodrug thereof, (v) a metabolite thereof and/or (vi) a salt of any of (i)-(v), comprised in the delayed release component or composition.

In another embodiment, the amount of (i) pyridoxine (ii) an analog thereof, (iii) a derivative thereof, (iv) a prodrug thereof, (v) a metabolite thereof and/or (vi) a salt of any of (i)-(v), comprised in the immediate release component or composition is substantially equivalent to the amount of (i) pyridoxine (ii) an analog thereof, (iii) a derivative thereof, (iv) a prodrug thereof, (v) a metabolite thereof and/or (vi) a salt of any of (i)-(v), comprised in the delayed release component or composition.

In an embodiment, the ratio, by weight, of the amount of (i) doxylamine, (ii) an analog thereof, (iii) a derivative thereof, (iv) a prodrug thereof, (v) a metabolite thereof and/or (vi) a salt of any of (i)-(v), in the immediate release component or composition to the amount of (i) doxylamine, (ii) an analog thereof, (iii) a derivative thereof, (iv) a prodrug thereof, (v) a metabolite thereof and/or (vi) a salt of any of (i)-(v); comprised in the delayed release component or composition is from about 5:0 to about 0:5. In further embodiments, the ratio is from about 4:0 to about 0:4, from about 3:0 to about 0:3, or from about 2:0 to about 0:2. In further embodiments, the ratio is from about 4:1 to about 1:4, from about 3:1 to about 1:3, or from about 2:1 to about 1:2.

In an embodiment, the ratio, by weight, of the amount of (i) pyridoxine, (ii) an analog thereof, (iii) a derivative thereof, (iv) a prodrug thereof, (v) a metabolite thereof and/or (vi) a salt of any of (i)-(v); comprised in the immediate release component or composition to the amount of (i) pyridoxine, (ii) an analog thereof, (iii) a derivative thereof, (iv) a prodrug thereof, (v) a metabolite thereof and/or (vi) a salt of any of (i)-(v); comprised in the delayed release component or composition, is from about 5:0 to about 0:5. In further embodiments, the ratio is from about 4:0 to about 0:4, from about 3:0 to about 0:3, or from about 2:0 to about 0:2. In further embodiments, the ratio is from about 4:1 to about 1:4, from about 3:1 to about 1:3, or from about 2:1 to about 1:2.

In another aspect, the present invention provides the use of the above-mentioned dual release oral dosage system or dual release oral dosage form as a medicament.

In another aspect, the present invention provides the use of the above-mentioned dual release oral dosage system or dual release oral dosage form for the preparation of a medicament.

In another aspect, the present invention provides the use of the above-mentioned dual release oral dosage system or dual release oral dosage form, for alleviating the symptoms of nausea and vomiting in a mammal.

In another aspect, the present invention provides the use of the above-mentioned dual release oral dosage system or dual release oral dosage form, for the preparation of a medicament for alleviating the symptoms of nausea and vomiting in a mammal.

In another aspect, the present invention provides the use of the above-mentioned dual release oral dosage system or dual release oral dosage form, for alleviating the symptoms of nausea and vomiting of human pregnancy (NVP).

In another aspect, the present invention provides the use of the above-mentioned dual release oral dosage system or dual release oral dosage form, for the preparation of a medicament for alleviating the symptoms of nausea and vomiting of human pregnancy.

In another aspect, the present invention provides the above-mentioned dual release oral dosage system or dual release oral dosage form for use as a medicament.

In another aspect, the present invention provides the above-mentioned dual release oral dosage system or dual release oral dosage form for use in the preparation of a medicament.

In another aspect, the present invention provides the above-mentioned dual release oral dosage system or dual release oral dosage form for use in alleviating the symptoms of nausea and vomiting in a mammal.

In another aspect, the present invention provides the above-mentioned dual release oral dosage system or dual release oral dosage form, for use in the preparation of a medicament for alleviating the symptoms of nausea and vomiting in a mammal.

In another aspect, the present invention provides the above-mentioned dual release oral dosage system or dual release oral dosage form, for use in alleviating the symptoms of nausea and vomiting of human pregnancy.

In another aspect, the present invention provides the above-mentioned dual release oral dosage system or dual release oral dosage form, for use in the preparation of a medicament alleviating the symptoms of nausea and vomiting of human pregnancy.

In an embodiment, the above-mentioned dual release oral dosage system or dual release oral dosage form is for administration under fasted conditions.

In another embodiment, the above-mentioned dual release oral dosage system or dual release oral dosage form is for administration under fed conditions.

In an aspect, the present invention provides a method for alleviating the symptoms of nausea and vomiting in a mammal, the method comprising administering the above-mentioned dual release oral dosage system or dual release oral dosage form, to a mammal in need thereof.

In an aspect, the present invention provides a method for alleviating the symptoms of nausea and vomiting during in human pregnancy, the method comprising administering the above-mentioned dual release oral dosage system or dual release oral dosage form, to a pregnant human female in need thereof.

In an embodiment, the above-mentioned dual release oral dosage system or dual release oral dosage form is administered under fasted conditions.

In another embodiment, the above-mentioned dual release oral dosage system or dual release oral dosage form is administered under fed conditions.

In another aspect, the present invention provides a kit for use in alleviating the symptoms of nausea and vomiting in a mammal, the kit comprising the above-mentioned dual release oral dosage system or dual release oral dosage form.

In an embodiment, the above-mentioned kit further comprises instructions for use of the dual release oral dosage system or the dual release oral dosage form for alleviating the symptoms of nausea and vomiting in a mammal.

In another aspect, the present invention provides a kit for use in alleviating the symptoms of nausea and vomiting of human pregnancy, the kit comprising the above-mentioned dual release oral dosage system or dual release oral dosage form.

In an embodiment, the above-mentioned kit further comprises instructions for use of the dual release oral dosage system or the dual release oral dosage form for alleviating the symptoms of nausea and vomiting in human pregnancy.

In an embodiment, the above-mentioned kit further comprises instructions for administration of the dual release oral dosage system or the dual release oral dosage form under fasted conditions.

In another embodiment, the above-mentioned kit further comprises instructions for administration of the dual release oral dosage system or the dual release oral dosage form under fed conditions.

In an embodiment, the above-mentioned mammal is a human. In an embodiment, the mammal is female. In a further embodiment, the mammal is a human female, in a further embodiment, a pregnant human female.

The following is a non-restrictive description of specific embodiments thereof, given by way of example with reference to the accompanying drawings.

BRIEF DESCRIPTION OF THE DRAWINGS

In the appended drawings:

FIG. 2 shows pharmacokinetic parameters for doxylamine (Doxy), pyridoxine, pyridoxal and pyridoxal 5-phosphate (PLP) in the fasted and fed states for a single dosage and multi-dosage of Diclectin®; Data are from a bioavailability study in 42 healthy women;

FIGS. 3A and 3B show a comparison of certain pharmacokinetic parameters for doxylamine (FIG. 3A) and pyridoxine (FIG. 3B) under fed and fasting conditions following Diclectin® administration in healthy women;

FIG. 4 shows the dose accumulation of the current formulation of Diclectin® in healthy women; the Accumulation index (AI) calculated as 1/(1-e-kel*24). Multi-dose study done in 18 healthy female subjects according to the following dosage schedule: Day 1: 20 mg (single dose), Day 2-17: 20 mg+10 mg+10 mg (multi-dose, 10 pm, 8 am and 4 pm) and Day 18: 20 mg (final dose); Doxy, doxylamine; PYR, pyridoxine; PYL, pyridoxal; PLP, pyridoxal 5-phosphate; PYM, pyridoxamine; PMP, pyridoxamine 5-phosphate;

FIG. 5 shows pharmacokinetics data for doxylamine and pyridoxine obtained in several bioavailability (BA) studies of the current formulation of Diclectin® in healthy women;

DESCRIPTION OF ILLUSTRATIVE EMBODIMENTS

Figure 1:
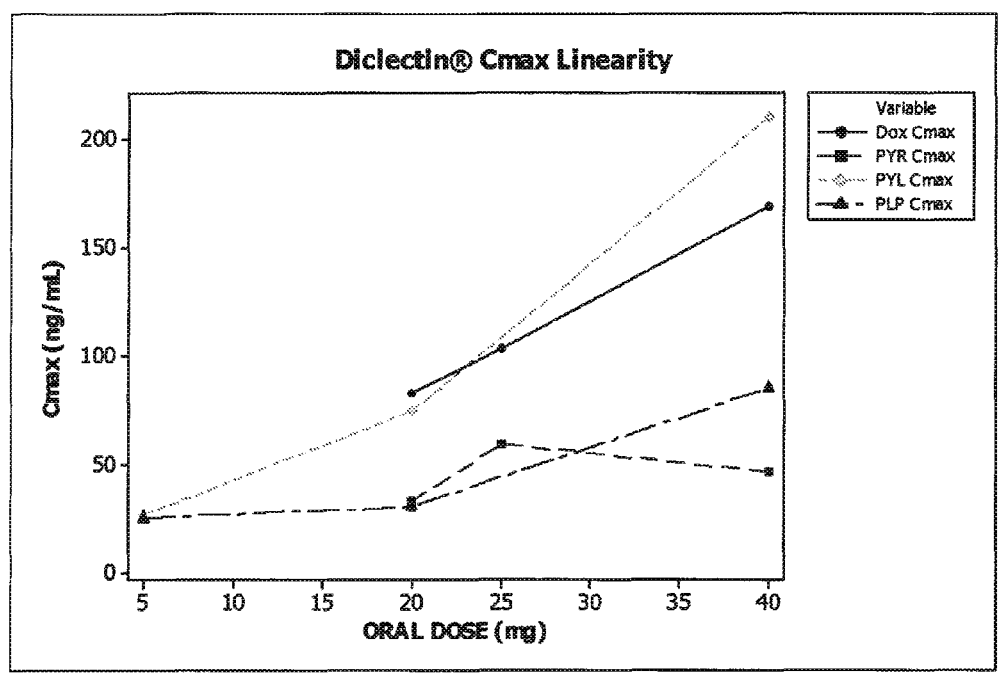
FIG. 1 shows studies of Diclectin® $C_{max}$ linearity. Data are from bioavailability studies in healthy volunteers. 5 mg: 12 healthy men, 20 mg: 42 healthy women, 25 mg: 12 healthy women, 40 mg: 18 healthy women.

The studies described herein show that a dual release oral dosage form of one or more of doxylamine and/or a doxylamine salt and one or more of pyridoxine and/or a pyridoxine salt and/or a pyridoxine metabolite and/or a salt of a pyridoxine metabolite, comprising an immediate release composition and a delayed release composition, exhibits an improved pharmacokinetics profile relative to the currently used Diclectin® formulation (the currently used Diclectin® formulation is a delayed release formulation containing 10 mg doxylamine succinate and 10 mg pyridoxine HCl).

In an aspect, the present invention provides a dual release oral dosage system comprising (a) a doxylamine component (or compound), i.e. one or more of (i) doxylamine, (ii) an analog thereof, (iii) a derivative thereof, (iv) a prodrug thereof, (v) a metabolite thereof and (vi) a salt of any of (i)-(v); and (b) a pyridoxine component (or compound), i.e. one or more of (i) pyridoxine, (ii) an analog thereof, (iii) a derivative thereof, (iv) a prodrug thereof, (v) a metabolite thereof and (vi) a salt of any of (i)-(v), said dual release oral dosage system comprising:

(A) an immediate release component comprising:
(a) one or more of (i) doxylamine, (ii) an analog thereof, (iii) a derivative thereof, (iv) a prodrug thereof, (v) a metabolite thereof and (vi) a salt of any of (i)-(v); and/or
(b) one or more of (i) pyridoxine, (ii) an analog thereof, (iii) a derivative thereof, (iv) a prodrug thereof, (v) a metabolite thereof and (vi) a salt of any of (i)-(v); and (B) a delayed release component comprising:
(a) one or more of (i) doxylamine, (ii) an analog thereof, (iii) a derivative thereof, (iv) a prodrug thereof, (v) a metabolite thereof and/or (vi) a salt of any of (i)-(v); and/or
(b) one or more of (i) pyridoxine, (ii) an analog thereof, (iii) a derivative thereof, (iv) a prodrug thereof, (v) a metabolite thereof and (vi) a salt of any of (i)-(v);

wherein said immediate release component is for effecting release of the one or more of (i) doxylamine, (ii) an analog thereof, (iii) a derivative thereof, (iv) a prodrug thereof, (v) a metabolite thereof and (vi) a salt of any of (i)-(v) and/or the one or more of (i) pyridoxine, (ii) an analog thereof, (iii) a derivative thereof, (iv) a prodrug thereof, (v) a metabolite thereof and (vi) a salt of any of (i)-(v), which begins prior to release of the one or more of (i) doxylamine, (ii) an analog thereof, (iii) a derivative thereof, (iv) a prodrug thereof, (v) a metabolite thereof, and/or the one or more of (i) pyridoxine, (ii) an analog thereof, (iii) a derivative thereof, (iv) a prodrug thereof, (v) a metabolite thereof and (vi) a salt of any of (i)-(v), from said delayed release component, within the gastrointestinal tract.

The term "doxylamine component" (or "doxylamine compound") as used herein refers to doxylamine, doxylamine analogs, derivatives, prodrugs, metabolites and/or salts. The term "pyridoxine component" (or "pyridoxine compound") as used herein refers to pyridoxine, pyridoxine analogs, derivatives, prodrugs, metabolites and/or salts.

The term "analog" or "derivative" as used herein refers to a different compound having a structure similar to that of the "parent" compound (e.g., doxylamine or pyridoxine) but differing from the parent compound in structure (e.g., replacement of one or more atoms by an atom of a different element, presence or absence of a particular group, etc.). An analog/derivative typically exhibits an overall biological effect that is similar to that of the "parent" compound but may differ in one or more physicochemical and/or pharmacokinetic properties (potency, stability, solubility, absorption, in vivo half-life, in vivo distribution, etc.).

"Prodrug" as used herein refers to a compound for administration (which is e.g., in an inactive, or significantly less active form) in a form that, following administration, undergoes chemical conversion by metabolic processes to be transformed into a compound to effect the desired pharmacological activity (e.g., to become an active, or more active, pharmacological agent).

"Metabolite" as used herein refers to a compound resulting from a biochemical conversion of a first compound by metabolic processes/pathways in vivo. A metabolite may differ in one or more physicochemical and/or pharmacokinetic properties (potency, stability, solubility, absorption, in vivo half-life, in vivo distribution, etc.) as compared to the first compound (which may be a prodrug or an active agent). If its structure is known, such a metabolite can be prepared in vitro and administered directly to a subject to exert a biological effect. A given metabolite may itself be metabolized through metabolic processes/pathways, thus resulting in one or more further metabolites that may differ in more or more physicochemical and/or pharmacokinetic properties as compared to the "first" metabolite.

As used herein the term "pharmaceutically acceptable salt" refers to a salt of a compound (an active ingredient) that retains the biological activity of the parent compound, and which is not biologically or otherwise undesirable, i.e., is a type of salt and/or is for use in an amount which is not toxic to the subject. In the case of a pregnant human female subject, the pharmaceutically acceptable salt is in concentrations that is not toxic to the embryo or fetus, (i.e., a pharmaceutical salt which is acceptable for administration to a pregnant female) and not contraindicated for use in human pregnancy. Thus, in dosage forms for administration to pregnant subjects, pharmaceutically acceptable salts that have teratogenic properties are excluded.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid. In an embodiment, the pharmaceutically acceptable salt of doxylamine is doxylamine succinate.

In an embodiment, the immediate release component and the delayed release component comprise the same doxylamine, analog thereof, derivative thereof, prodrug thereof, metabolite thereof or salt thereof (or the same combination of doxylamine, analog thereof, derivative thereof, prodrug thereof, metabolite thereof and/or salt thereof). In another embodiment, the immediate release component and the delayed release component comprise different doxylamine, analog thereof, derivative thereof, prodrug thereof, metabolite thereof or salt thereof (or a different combination of doxylamine, analog thereof, derivative thereof, prodrug thereof, metabolite thereof and/or salt thereof). In an embodiment, the immediate release component and/or the delayed release component comprise only one of doxylamine, an analog thereof, a derivative thereof, a prodrug thereof, a metabolite thereof or a salt thereof. In an embodiment, the immediate release component and/or the delayed release component comprise doxylamine succinate. In an embodiment, only the immediate release component comprises doxylamine, an analog thereof, a derivative thereof, a prodrug thereof, a metabolite thereof and/or a salt thereof. In another embodiment, only the delayed release component comprises doxylamine, an analog thereof, a derivative thereof, a prodrug thereof, a metabolite thereof and/or a salt thereof.

In an embodiment, the above-mentioned immediate release component and/or delayed release component comprise pyridoxine (PYR) and/or a further medicinal ingredient, such as one or more metabolites of PYR, such as pyridoxine phosphate (PYP), pyridoxal (PYL), pyridoxal 5-phosphate (PLP), pyridoxamine (PYM), pyridoxamine 5-phosphate (PMP), and/or one or more pharmaceutically acceptable salts of PYR, PYP, PYL, PLP, PYM and/or PMP. In an embodiment, the immediate release component and/or the delayed release component comprise pyridoxal (in addition to one or more of (i) doxylamine, (ii) an analog thereof, (iii) a derivative thereof, (iv) a prodrug thereof, (v) a metabolite thereof and (vi) a salt of any of (i)-(v)). Pyridoxine analogs, derivatives, prodrugs, metabolites and salts include, for example, pharmaceutically acceptable esters or amines of pyridoxine, pyridoxine hydrochloride, pyridoxine phosphate, pyridoxal, pyridoxal phosphate, pyridoxal calcium phosphate, pyridoxal hydrochloride, pyridoxamine, or pyridoxamine dihydrochloride. In an embodiment, the pharmaceutically acceptable salt of pyridoxine is pyridoxine hydrochloride. In an embodiment, the immediate release component and the delayed release component comprise the same pyridoxine, metabolite thereof or salt thereof (or the same combination of pyridoxine, metabolite thereof and/or salt thereof). In another embodiment, the immediate release component and the delayed release component comprise a different pyridoxine, prodrug, metabolite thereof or salt thereof (or a different combination of pyridoxine, prodrug thereof and/or metabolite thereof and/or salt thereof). In an embodiment, only the immediate release component comprises (i) pyridoxine, (ii) an analog thereof, (iii) a derivative thereof, (iv) a prodrug thereof, (v) a metabolite thereof and/or (vi) a salt of any of (i)-(v). In another embodiment, only the delayed release component comprises (i) pyridoxine, (ii) an analog thereof, (iii) a derivative thereof, (iv) a prodrug thereof, (v) a metabolite thereof and/or (vi) a salt of any of (i)-(v).

For example, the immediate release component and/or the delayed release component may comprise PYR, PYL, PLP, PYM or PMP, or PYP, or any combination thereof (e.g., PYR+PYL, PYR+PLP, PYR+PYM, PYR+PMP, PYR+PYP, PYL+PLP, PYL+PYM, PYL+PMP, PLP+PYM, PLP+PMP, PYL+PYP, PYR+PYL+PLP, PYR+PYL+PYM, PYR+PYL+PMP, PYL+PLP+PYM, PYR+PYL+PYP, PYR+PLP+PMP, PYR+PLP+PYP, PYR+PYM+PMP, PLP+PYM+PYP, etc.). The immediate release component and/or the delayed release component may further comprise one or more of (i) doxylamine, (ii) an analog thereof, (iii) a derivative thereof, (iv) a prodrug thereof, (v) a metabolite thereof and (vi) a salt of any of (i)-(v).

In an embodiment, the immediate release component (A) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v), and the delayed release component (B) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v).

In another embodiment, the immediate release component (A) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v), and the delayed release component (B) comprises one or more of (i) doxylamine, (ii) an analog thereof, (iii) a derivative thereof, (iv) a prodrug thereof, (v) a metabolite thereof and (vi) a salt of any of (i)-(v).

In another embodiment, the immediate release component (A) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v), and the delayed release component (B) comprises one or more of (i) pyridoxine (ii) an analog thereof, (iii) a derivative thereof, (iv) a prodrug thereof, (v) a metabolite thereof and (vi) a salt of any of (i)-(v).

In another embodiment, the immediate release component (A) comprises one or more of (i) doxylamine, (ii) an analog thereof, (iii) a derivative thereof, (iv) a prodrug thereof, (v) a metabolite thereof and (vi) a salt of any of (i)-(v); and the delayed release component (B) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v).

In another embodiment, the immediate release component (A) comprises one or more of (i) pyridoxine (ii) an analog thereof, (iii) a derivative thereof, (iv) a prodrug thereof, (v) a metabolite thereof and (vi) a salt of any of (i)-(v), and the delayed release component (B) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v).

In another embodiment, the immediate release component (A) comprises one or more of (i) doxylamine, (ii) an analog thereof, (iii) a derivative thereof, (iv) a prodrug thereof, (v) a metabolite thereof and (vi) a salt of any of (i)-(v); and the delayed release component (B) comprises one or more of (i) pyridoxine (ii) an analog thereof, (iii) a derivative thereof, (iv) a prodrug thereof, (v) a metabolite thereof and (vi) a salt of any of (i)-(v).

In an embodiment, the immediate release component (A) comprises one or more of (i) pyridoxine (ii) an analog thereof, (iii) a derivative thereof, (iv) a prodrug thereof, (v) a metabolite thereof and (vi) a salt of any of (i)-(v), and the delayed release component (B) comprises one or more of (i) doxylamine, (ii) an analog thereof, (iii) a derivative thereof, (iv) a prodrug thereof, (v) a metabolite thereof and (vi) a salt of any of (i)-(v).

In an embodiment, the immediate release component (A) comprises one or more of (i) doxylamine, (ii) an analog thereof, (iii) a derivative thereof, (iv) a prodrug thereof, (v) a metabolite thereof and (vi) a salt of any of (i)-(v), and one or more of (i) pyridoxine (ii) an analog thereof, (iii) a derivative thereof, (iv) a prodrug thereof, (v) a metabolite thereof and (vi) a salt of any of (i)-(v); and the delayed release component (B) comprises doxylamine succinate and pyridoxine-HCl. In a further embodiment, the immediate release component (A) comprises doxylamine succinate and pyridoxal; and the delayed release component (B) comprises doxylamine succinate and pyridoxine-HCl.

The present invention also provides a dual release oral dosage system comprising:

(A) an immediate release component comprising:
(a) one or more of (i) doxylamine, (ii) an analog thereof, (iii) a derivative thereof, (iv) a prodrug thereof, (v) a metabolite thereof and (vi) a salt of any of (i)-(v); and/or
(b) one or more of (i) pyridoxine (ii) an analog thereof, (iii) a derivative thereof, (iv) a prodrug thereof, (v) a metabolite thereof and (vi) a salt of any of (i)-(v); and (B) a delayed release component comprising:
(a) one or more of (i) doxylamine, (ii) an analog thereof, (iii) a derivative thereof, (iv) a prodrug thereof, (v) a metabolite thereof and (vi) a salt of any of (i)-(v); and/or (b) one or more of (i) pyridoxine (ii) an analog thereof, (iii) a derivative thereof, (iv) a prodrug thereof, (v) a metabolite thereof and (vi) a salt of any of (i)-(v); and wherein said immediate release component is for effecting release of the one or more of (i) doxylamine, (ii) an analog thereof, (iii) a derivative thereof, (iv) a prodrug thereof, (v) a metabolite thereof and (vi) a salt of any of (i)-(v) and/or the one or more of (i) pyridoxine, (ii) an analog thereof, (iii) a derivative thereof, (iv) a prodrug thereof, (v) a metabolite thereof and (vi) a salt of any of (i)-(v), which begins prior to release of the one or more of (i) doxylamine, (ii) an analog thereof, (iii) a derivative thereof, (iv) a prodrug thereof, (v) a metabolite thereof, and/or the one or more of (i) pyridoxine, (ii) an analog thereof, (iii) a derivative thereof, (iv) a prodrug thereof, (v) a metabolite thereof and (vi) a salt of any of (i)-(v), from said delayed release component, within the gastrointestinal tract.

In an embodiment, the above-mentioned system provides a maximum daily dosage of the doxylamine, analog thereof, derivative thereof, prodrug thereof, metabolite thereof and/or salt thereof of about 40 to about 80 mg, for example about 50 to about 70 mg, in a further embodiment about 60 mg.

In an embodiment, the above-mentioned system provides a daily dosage of the doxylamine, analog thereof, derivative thereof, prodrug thereof, metabolite thereof and/or salt thereof of about 10 mg to about 40 mg, in a further embodiment form about 20 to about 40 mg, for example about 20, 25, 30, 35 or 40 mg. In an embodiment, the above-mentioned system provides a daily dosage of the doxylamine, analog thereof, derivative thereof, prodrug thereof, metabolite thereof and/or salt thereof of about 40 mg.

In an embodiment, the above-mentioned system provides an average $C_{max}$ of the doxylamine, analog thereof, derivative thereof, prodrug thereof, metabolite thereof and/or salt thereof, of up to about 250 ng/ml.

In an embodiment, the above-mentioned system provides an average $C_{max}$ of the doxylamine, analog thereof, derivative thereof, prodrug thereof, metabolite thereof and/or salt thereof, of about 70 ng/ml to about 250 ng/ml, for example of about 70, 75, 80, 85, 90, 95, 100, 105, 110, 115, 120, 125, 130, 140, 150 or 160 to about 170, 180, 190, 200, 210, 220, 230, 240 or 250 ng/ml.

In an embodiment, the above-mentioned system provides a maximum daily dosage of the pyridoxine, analog thereof, derivative thereof, prodrug thereof, metabolite thereof and/or salt thereof, of about 90 to about 110 mg, for example about 100 mg.

In an embodiment, the above-mentioned system provides a daily dosage of the pyridoxine, analog thereof, derivative thereof, prodrug thereof, metabolite thereof and/or salt thereof, of about 1 mg to about 100 mg, for example, from about 5, 10, 15, 20, 25 to about 30, 35, 40, 45, 50, 55, 60, 65, 70, 80, 85, 90, or 95 mg. In an embodiment, the above-mentioned system provides a daily dosage of the pyridoxine, analog thereof, derivative thereof, prodrug thereof, metabolite thereof and/or salt thereof, of about 60 mg.

In an embodiment, the above-mentioned system provides an average $C_{max}$ of the pyridoxine, analog thereof, derivative thereof, prodrug thereof, metabolite thereof and/or salt thereof, of up to about 300 ng/ml.

In an embodiment, the above-mentioned system provides an average $C_{max}$ of the pyridoxine, analog thereof, derivative thereof, prodrug thereof, metabolite thereof and/or salt thereof, (e.g., PYR, PYL, PLP, PYM, PYP and/or PMP) of about 5 ng/ml to about 300 ng/ml, in further embodiments from about 10 to about 250 ng/ml, for example from about 10, 15, 20, 25, 30, 35, 40, 45, 50, 55, 60, 65, 70, 75 or 80 to about 100, 105, 110, 115, 120, 125, 130, 135, 140, 145, 150, 155, 160, 165, 170, 175, 180, 185, 190, 195, 200, 210, 220, 230, 240 or 250 ng/ml. In an embodiment, the above-mentioned system provides an average $C_{max}$ of the pyridoxine, derivative thereof, prodrug thereof, metabolite thereof and/or salt thereof, of about 40 to about 130 ng/ml, in a further embodiment of about 44 to about 128 ng/ml, for example about 85 ng/ml. In an embodiment, the pyridoxine metabolite is PLP.

In an embodiment, the above-mentioned dual release oral dosage system comprises at least two dual release oral dosage forms, wherein each of said oral dosage forms comprises:
 (A) an immediate release composition comprising:
  (a) one or more of (i) doxylamine, (ii) an analog thereof, (iii) a derivative thereof, (iv) a prodrug thereof, (v) a metabolite thereof and (vi) a salt of any of (i)-(v); and/or
  (b) one or more of (i) pyridoxine (ii) an analog thereof, (iii) a derivative thereof, (iv) a prodrug thereof, (v) a metabolite thereof and (vi) a salt of any of (i)-(v); and
 (B) a delayed release composition comprising:
  (a) one or more of (i) doxylamine, (ii) an analog thereof, (iii) a derivative thereof, (iv) a prodrug thereof, (v) a metabolite thereof and (vi) a salt of any of (i)-(v); and/or (b) one or more of (i) pyridoxine (ii) an analog thereof, (iii) a derivative thereof, (iv) a prodrug thereof, (v) a metabolite thereof and (vi) a salt of any of (i)-(v).

In another aspect, the present invention provides a dual release oral dosage form comprising (a) a doxylamine component, i.e. one or more of (i) doxylamine, (ii) an analog thereof, (iii) a derivative thereof, (iv) a prodrug thereof, (v) a metabolite thereof and (vi) a salt of any of (i)-(v); and (b) a pyridoxine component, i.e. one or more of (i) pyridoxine, (ii) an analog thereof, (iii) a derivative thereof, (iv) a prodrug thereof, (v) a metabolite thereof and (vi) a salt of any of (i)-(v), said dual release oral dosage form comprising:
 (A) an immediate release composition comprising:
  (a) one or more of (i) doxylamine, (ii) an analog thereof, (iii) a derivative thereof, (iv) a prodrug thereof, (v) a metabolite thereof and (vi) a salt of any of (i)-(v); and/or
  (b) one or more of (i) pyridoxine (ii) an analog thereof, (iii) a derivative thereof, (iv) a prodrug thereof, (v) a metabolite thereof and (vi) a salt of any of (i)-(v); and
 (B) a delayed release composition comprising:
  (a) one or more of (i) doxylamine, (ii) an analog thereof, (iii) a derivative thereof, (iv) a prodrug thereof, (v) a metabolite thereof and (vi) a salt of any of (i)-(v); and/or (b) one or more of (i) pyridoxine, ((ii) an analog thereof, (iii) a derivative thereof, (iv) a prodrug thereof, (v) a metabolite thereof and (vi) a salt of any of (i)-(v);

wherein said immediate release composition is for effecting release of (a) and/or (b), which begins prior to release of (a) and/or (b) from said delayed release composition, within the gastrointestinal tract.

The terms "oral dosage form," "unit dose form," and the like are used interchangeably, and have their normal meaning in the art (i.e., refer to a pharmaceutical composition in the form of a tablet, capsule, caplet, gelcap, geltab, pill, flowable powder and the like).

In an embodiment, the above-mentioned composition comprises a pharmaceutically acceptable salt of doxylamine, in a further embodiment doxylamine succinate. In an embodiment, the immediate release composition and the delayed release composition comprise the same doxylamine, analog thereof, derivative thereof, prodrug thereof, metabolite thereof or salt thereof (or the same combination of doxylamine, analog thereof, derivative thereof, prodrug thereof, metabolite thereof and/or salt thereof). In another embodiment, the immediate release composition and the delayed release composition comprise different doxylamine, analog thereof, derivative thereof, prodrug thereof, metabolite thereof or salt thereof (or a different combination of doxylamine, analog thereof, derivative thereof, prodrug thereof, metabolite thereof and/or salt thereof). In an embodiment, the immediate release composition and/or the delayed release composition comprise only one doxylamine, analog thereof, derivative thereof, prodrug thereof, metabolite thereof or salt thereof. In an embodiment, only the immediate release composition comprises doxylamine, an analog thereof, a derivative thereof, a prodrug thereof, a metabolite thereof and/or a salt thereof. In another embodiment, only the delayed release composition comprise doxylamine, an analog thereof, a derivative thereof, a prodrug thereof, a metabolite thereof and/or a salt thereof. In an embodiment, the immediate release composition and/or the delayed release composition comprise doxylamine succinate.

In an embodiment, the above-mentioned immediate release composition and/or delayed release composition comprise pyridoxine (PYR) and/or a further medicinal ingredient, such as one or more metabolites of PYR, such as pyridoxine phosphate (PYP), pyridoxal (PYL), pyridoxal 5-phosphate (PLP), pyridoxamine (PYM), pyridoxamine 5-phosphate (PMP), and/or one or more pharmaceutically acceptable salts of PYR, PYP, PYL, PLP, PYM and/or PMP. In an embodiment, the immediate release composition and the delayed release composition comprise the same pyridoxine, metabolite thereof or salt thereof (or the same combination of pyridoxine, metabolite thereof and/or salt thereof). In another embodiment, the immediate release composition and the delayed release composition comprise different pyridoxine, metabolite thereof or salt thereof (or a different combination of pyridoxine, metabolite thereof and/or salt thereof). In an embodiment, only the immediate release composition comprises (i) pyridoxine, (ii) an analog thereof, (iii) a derivative thereof, (iv) a prodrug thereof, (v) a metabolite thereof and/or (vi) a salt of any of (i)-(v). In another embodiment, only the delayed release composition comprises (i) pyridoxine, (ii) an analog thereof, (iii) a derivative thereof, (iv) a prodrug thereof, (v) a metabolite thereof and/or (vi) a salt of any of (i)-(v).

For example, the immediate release composition and/or the delayed release composition may independently comprise (in addition to (I) doxylamine, (ii) an analog thereof, (iii) a derivative thereof, (iv) a prodrug thereof, (v) a metabolite thereof and (vi) a salt of any of (i)-(v)) PYR, PYL, PLP, PYM, PYP or PMP, or any combination thereof (e.g., PYR+PYL, PYR+PLP, PYR+PYM, PYR+PMP, PYL+PLP, PYL+PYP, PYL+PYM, PYL+PMP, PLP+PYM, PLP+PMP, PLP+PYP PYR+PYL+PLP, PYR+PYL+PYM, PYR+PYL+PMP, PYL+PLP+PYM, PYR+PYL+PYP, PYR+PLP+PMP, PYR+PYM+PMP, PLP+PYM+PMP, etc.). The immediate release component and/or the delayed release component may further comprise one or more of (i) doxylamine, (ii) an analog thereof, (iii) a derivative thereof, (iv) a prodrug thereof, (v) a metabolite thereof and (vi) a salt of any of (i)-(v).

In an embodiment, the immediate release composition (A) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v), and the delayed release composition (B) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v).

In another embodiment, the immediate release composition (A) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v), and the delayed release composition (B) comprises one or more of (i) doxylamine, (ii) an analog thereof, (iii) a derivative thereof, (iv) a prodrug thereof, (v) a metabolite thereof and (vi) a salt of any of (i)-(v).

In another embodiment, the immediate release composition (A) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v), and the delayed release composition (B) comprises one or more of (I) pyridoxine (ii) an analog thereof, (iii) a derivative thereof, (iv) a prodrug thereof, (v) a metabolite thereof and (vi) a salt of any of (i)-(v).

In another embodiment, the immediate release composition (A) comprises one or more of (i) doxylamine, (ii) an analog thereof, (iii) a derivative thereof, (iv) a prodrug thereof, (v) a metabolite thereof and (vi) a salt of any of (i)-(v); and the delayed release composition (B) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v).

In another embodiment, the immediate release composition (A) comprises one or more of (i) pyridoxine (ii) an analog thereof, (iii) a derivative thereof, (iv) a prodrug thereof, (v) a metabolite thereof and (vi) a salt of any of (i)-(v), and the delayed release composition (B) comprises (a) one or more of (i) doxylamine, (ii) an analog thereof, (iii) a derivative thereof, (iv) a prodrug thereof, (v) a metabolite thereof and (vi) a salt of any of (i)-(v); and (b) one or more of (i) pyridoxine (ii) an analog thereof, (iii) a derivative thereof, (iv) a prodrug thereof, (v) a metabolite thereof and (vi) a salt of any of (i)-(v).

In another embodiment, the immediate release composition (A) comprises one or more of (i) doxylamine, (ii) an analog thereof, (iii) a derivative thereof, (iv) a prodrug thereof, (v) a metabolite thereof and (vi) a salt of any of (i)-(v); and the delayed release composition (B) comprises one or more of (i) pyridoxine (ii) an analog thereof, (iii) a derivative thereof, (iv) a prodrug thereof, (v) a metabolite thereof and (vi) a salt of any of (i)-(v).

In an embodiment, the immediate release composition (A) comprises one or more of (i) pyridoxine (ii) an analog thereof, (iii) a derivative thereof, (iv) a prodrug thereof, (v) a metabolite thereof and (vi) a salt of any of (i)-(v), and the delayed release composition (B) comprises one or more of (i) doxylamine, (ii) an analog thereof, (iii) a derivative thereof, (iv) a prodrug thereof, (v) a metabolite thereof and (vi) a salt of any of (i)-(v).

In an embodiment, the above-mentioned system consists of 2, 3 or 4 dual release oral dosage forms. In a further embodiment, the above-mentioned system consists of 2 dual release oral dosage forms. In another embodiment, the above-mentioned system consists of 3 dual release oral dosage forms. In yet another embodiment, the above-mentioned system consists of 4 dual release oral dosage forms.

In an embodiment, at least two of the dual release oral dosage forms are the same, i.e. same active ingredients, same doses, same excipients, same unit form (e.g., tablet). In another embodiment, all of the dual release oral dosage forms are the same.

In another embodiment, at least two of the dual release oral dosage forms are different, i.e., different active ingredients (the doxylamine, analog thereof, derivative thereof, prodrug thereof, metabolite thereof and/or salt thereof, and/or pyridoxine, metabolite thereof and/or salt thereof, are different), different amounts of one or more of the active ingredients (e.g., the total dose, the doses in the immediate release formulation and/or the dose in the delayed release formulation), different excipients, and/or different unit form (e.g., tablet vs. capsule). In another embodiment, all of the dual release oral dosage forms are different. For example, in a system consisting of two dual release oral dosage forms, the first oral dosage form may comprise a doxylamine salt (e.g., doxylamine succinate) and PYR, and the second oral dosage form may comprise the same doxylamine salt (e.g., doxylamine succinate) but with a pyridoxine metabolite (e.g., PLP) or a combination of pyridoxine and a pyridoxine metabolite (e.g., PYR+PLP). In another example, the amount of the doxylamine, analog thereof, derivative thereof, prodrug thereof, metabolite thereof and/or salt thereof in the immediate release composition of the first and second oral dosage forms may be 5 mg and 2.5 mg, respectively.

In an embodiment, each of the different dual release oral dosage forms comprises an identifying characteristic (e.g., shape, size, color, an identifying mark, any combination thereof) such that said different dual release oral dosage forms can be distinguished from one another.

Immediate Release

The term "immediate release composition" as used herein refers to a composition of a dosage form that is formulated to release substantially all the active ingredient(s) in a relatively short period on administration with no enhanced, delayed or extended release effect. In some embodiments, the relatively short period can be, for example, within about 0.1 to about 2 hours, e.g., about 10, 15, 20, 30, 40, 60, 90 or 120 minutes. In some embodiments, the immediate release component releases a majority of the active ingredient(s), e.g., at least about 50%, 60%, 70%, 80%, 90%, 95% or 99% of active ingredient(s) from within the dosage form within such a relatively short period after administration. For example, about 80% of the drug can be released within about 30 or 40 minutes after administration, as measured by standard dissolution assays such as those described herein. In an embodiment, the immediate release composition is for effecting release substantially (at least about 90, 91, 92, 93, 94, 95, 96, 97, 98 or 99% is released) within the stomach.

Delayed Release

The term "delayed release composition" as used herein refers to a composition of a dosage form that is formulated so as to have zero or relatively low release of the active ingredient(s) during a period after administration to the subject. The period is typically in the range of about 0.5 to 12 hours, for example in the range of about 1 or 2 hours to about 6, 7, 8 or 9 hours, such as about 1, 2, 3, 4, 5, 6, 7, 8, or 9 hours. In embodiments, the delayed release begins after a period that is from about 2 hours to about 3 hours, or from about 3 hours to about 4 hours, or from about 4 hours to about 5 hours, or from about 5 hours to about 6 hours, after administration. In an embodiment, the delayed release composition is for effecting release substantially within the intestine, i.e., so that there is no or substantially no (less than about 10, 9, 8, 7, 6, 5, 4, 3, 2, or 1%) release in the stomach.

In an embodiment, although the delayed release component from the unit dose form commences to dissolve at a later time point than the immediate release component, once release begins, the release pattern of the delayed release component is similar to the pattern of the immediate release component, described above. For example, a relatively short burst duration, for example less than 60 minutes, for instance less than about 50, 40, 30, 20, 15, 10, or 5 minutes, may be characteristic of both immediate release and delayed-burst release. Delayed-burst release can occur in a substantially unimpeded and/or relatively rapid manner once release begins. Many methods are known in the art for providing delayed-burst release, such as by diffusion, swelling, osmotic bursting or erosion (e.g., based on the inherent dissolution of the agent and incorporated excipients); certain methods are described below.

Coordination of Release

The immediate release and delayed release compositions result in two sequential releases of the active ingredients, the first release occurring relatively soon after administration and the second release coming later. The time period between the first immediate release of the active ingredients and the subsequent delayed release of the active ingredients can be referred to as the "release interval." In unit dose forms of the invention, the release interval can generally be in the range of about 0.5 to 12 hours, for example in the range of about 1 or 2 hours to about 6, 7, 8 or 9 hours, such as about 1, 2, 3, 4, 5, 6, 7, 8, or 9 hours. In embodiments, the delayed release begins after a period that is from about 2 hours to about 3 hours, or from about 3 hours to about 4 hours, or from about 4 hours to about 5 hours, or from about 5 hours to about 6 hours. Optionally, the delayed release is timed to occur at a time when the dosage form is found in the small intestine in fasting and/or fed subjects. The immediate release of active ingredients can for example occur within about 1 hour after administration, for example within about 30 minutes or within about 15 minutes. In an embodiment, the release rate of the doxylamine, analog thereof, derivative thereof, prodrug thereof, metabolite thereof and/or salt thereof is substantially similar (i.e., the difference is less than 10, 9, 8, 7, 6, 5, 4, 3, 2, or 1%) to that of the pyridoxine, metabolite thereof and/or salt thereof (in either one of, or both, the immediate and delayed release compositions). In an embodiment, the release rate of the doxylamine, analog thereof, derivative thereof, prodrug thereof, metabolite thereof and/or salt thereof is different than that of the pyridoxine, (ii) an analog thereof, (iii) a derivative thereof, (iv) a prodrug thereof, (v) a metabolite thereof and (vi) a salt of any of (i)-(v) (in either one of, or both, the immediate and delayed release compositions).

The release interval can be determined in vitro or in vivo. Although the plasma concentration of a drug can lag behind the actual time of release in the GI tract, the release interval can be approximately determined in vivo as the time interval between the $C_{max}$ (i.e., the maximum plasma concentration) of the active ingredient achieved by the immediate release component and the $C_{max}$ of the active ingredient achieved by the delayed release component. Alternatively, the release interval can be monitored through the increased plasma concentration of the active ingredient caused by delayed release following immediate release, compared to that achieved by only the immediate release of the active ingredient.

Release can also be assessed using commonly used in vitro dissolution assays. Generally an in vitro dissolution assay is carried out by placing the dosage form(s) (e.g., tablet(s)) in a known volume of dissolution medium in a container with a suitable stirring device. An aliquot of the medium is withdrawn at various times and analyzed for dissolved active substance to determine the rate of dissolution. In one approach, the dosage form (e.g., tablet) is placed into a vessel of a United States Pharmacopeia dissolution apparatus II (Paddles) containing 900 ml dissolution medium at 37° C. The paddle speed is 50, 75 or 100 RPM. Independent measurements are made for at least three (3) tablets, e.g., 6 tablets. The dissolution medium can be a neutral dissolution medium such as 50 mM potassium phosphate buffer, pH 7.2 ("neutral conditions") or water or an acidic medium such as 50 mM potassium (or sodium) acetate buffer, at pH 4.5. Typically a unit dose form is added to the vessel and dissolution is started. At specified times, e.g., 5, 10, 15, 20, 30, 45 or 60 minutes, an aliquot (e.g., 2 ml) of medium is withdrawn and the amount of active ingredient in solution is determined using routine analytical methods (e.g., HPLC).

By way of example, immediate release and/or delayed release of drug from the unit dosage form can be monitored using Apparatus II (Paddles) as described in U.S. Pharmacopeia, where the dissolution is conducted by placing one tablet into each of six vessels containing 900 ml of release media with temperature at 37° C. and speed of 100 rpm. Optionally, the release media of 0.1N Hydrochloric acid (pH 1.2 or 4.5) is used for stage 1 for 2 hours, and 0.2M tribasic sodium phosphate buffer adjusted to pH6.8 is used for stage 2 (Buffer stage) at 5, 10, 15, 20, 30, 45, 60, 90 and 120 minutes and assayed for drug content by HPLC. Further, various media for in vitro dissolution assays (e.g., simulated gastric fluid (SGF), simulated intestinal fluid (SIF), versions to simulate fed or fasting conditions (FeSSGF or FeSSIF for fed conditions, FaSSGF or FaSSIF for fasting conditions), etc.) are well known in the art.

Excipients

The active ingredients are formulated with one or more pharmaceutically acceptable excipients. An "excipient," as used herein, has its normal meaning in the art and is any ingredient of an oral dosage form that is not an active ingredient (drug) itself. Excipients include for example binders, lubricants, diluents, fillers, thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. In the case of a pregnant human female subject, the pharmaceutically acceptable excipient is also not toxic to the embryo or fetus, i.e., a pharmaceutical excipient suitable for administration to a pregnant female. Thus, in dosage forms for administration to pregnant subjects, pharmaceutically acceptable excipients that have teratogenic properties and/or that are contraindicated for use in pregnancy are excluded. Excipients are well known in the art, and the present system is not limited in these respects. See, for example, Remington's Pharmaceutical Sciences, 18th Edition, A. Gennaro, Ed., Mack Pub. Co. (Easton, Pa., 1990), Chapters 88-91. In certain embodiments, one or more formulations of the dosage form include excipients, including for example and without limitation, one or more binders (binding agents), thickening agents, surfactants, diluents, release-delaying agents, colorants, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill will also recognize, these terms are not necessarily mutually exclusive.

Useful diluents, e.g., fillers, employable in such formulations may include, for example and without limitation, dicalcium phosphate, calcium diphosphate, calcium carbonate, calcium sulfate, lactose, cellulose, kaolin, sodium chloride, starches, powdered sugar, colloidal silicon dioxide, titanium oxide, alumina, talc, colloidal silica, microcrystalline cellulose, silicified micro crystalline cellulose and combinations thereof. Fillers that can add bulk to tablets with minimal drug dosage to produce tablets of adequate size and weight include croscarmellose sodium NF/EP (e.g., Ac-Di-Sol); anhydrous lactose NF/EP (e.g., Pharmatose™ DCL 21); and/or povidone USP/EP. In an embodiment, the diluent or filler is microcrystalline cellulose.

Binder materials employable in such formulations may include, for example and without limitation, starches (including corn starch and pregelatinized starch), gelatin, sugars (including sucrose, glucose, dextrose and lactose), polyethylene glycol, povidone, waxes, and natural and synthetic gums, e.g., acacia sodium alginate, polyvinylpyrrolidone, cellulosic polymers (e.g., hydroxypropyl cellulose, hydroxypropyl methylcellulose, methyl cellulose, hydroxyethyl cellulose, carboxymethylcellulose, colloidal silicon dioxide NF/EP (e.g., Cab-O—Sil™ M5P), Silicified Microcrystalline Cellulose (SMCC), e.g., Silicified microcrystalline cellulose NF/EP (e.g., Prosolv™ SMCC 90), and silicon dioxide, mixtures thereof, and the like), veegum, and combinations thereof.

Useful lubricants employable in such formulations may include, for example, canola oil, glyceryl palmitostearate, hydrogenated vegetable oil (type I), magnesium oxide, magnesium stearate, mineral oil, poloxamer, polyethylene glycol, sodium lauryl sulfate, sodium stearate fumarate, stearic acid, talc and, zinc stearate, glyceryl behapate, magnesium lauryl sulfate, boric acid, sodium benzoate, sodium acetate, sodium benzoate/sodium acetate (in combination), DL leucine, calcium stearate, sodium stearyl fumarate, mixtures thereof, and the like. In an embodiment, the lubricant is magnesium stearate.

Bulking agents employable in these compositions may include, for example: microcrystalline cellulose, for example, AVICEL® (FMC Corp.) or EMCOCEL® (Mendell Inc.), which also has binder properties; dicalcium phosphate, for example, EMCOMPRESS® (Mendell Inc.); calcium sulfate, for example, COMPACTROL® (Mendell Inc.); and starches, for example, Starch 1500; and polyethylene glycols (CARBOWAX®).

Suitable disintegrating or dissolution promoting agents employable in such formulations may include, but are not limited to: starches, clays, celluloses, alginates, gums, crosslinked polymers, colloidal silicon dioxide, osmogens, mixtures thereof, and the like, such as crosslinked sodium carboxymethyl cellulose (AC-DI-SOL®), sodium croscarmelose, sodium starch glycolate (EXPLOTAB®, PRIMO JEL®) crosslinked polyvinylpolypyrrolidone (PLASONE-XL®), sodium chloride, sucrose, lactose and mannitol. In an embodiment, the disintegrating agent is sodium croscarmelose.

Antiadherents and glidants employable in such formulations may include talc, starches (e.g., cornstarch), celluloses, silicon dioxide, sodium lauryl sulfate, colloidal silica dioxide, and metallic stearates, among others.

Examples of silica flow conditioners include colloidal silicon dioxide, magnesium aluminum silicate and guar gum. In an embodiment, the silica flow conditioner is silicon dioxide.

Suitable surfactants employable in such formulations include pharmaceutically acceptable non-ionic, ionic and anionic surfactants. An example of a surfactant is sodium lauryl sulfate. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. If desired, flavoring, coloring and/or sweetening agents may be added as well.

Examples of stabilizing agents include acacia, albumin, polyvinyl alcohol, alginic acid, bentonite, dicalcium phosphate, carboxymethylcellulose, hydroxypropylcellulose, colloidal silicon dioxide, cyclodextrins, glyceryl monostearate, hydroxypropyl methylcellulose, magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol. In an embodiment, the stabilizing agent is magnesium trisilicate.

Optionally, a thickening agent can be added to provide the dosage form (e.g., tablet) with an accurately timed disintegration behavior. The dosage form optionally disintegrates at a rate which is sufficiently slow to permit it to be swallowed easily, but fast enough to give an excellent suspension in water within 60 seconds. The thickening agent can be for example talc USP/EP, a natural gum, such as guar gum or gum arabic, or a cellulose derivative such as microcrystalline cellulose NF/EP (e.g., Avicel™ PH 102), methylcellulose, ethylcellulose or hydroxyethylcellulose. A useful thickening agent is hydroxypropyl methylcellulose, an adjuvant which is available in various viscosity grades.

Similarly, suitable plasticizers employable in such formulations include: acetylated monoglycerides; these can be used as food additives; Alkyl citrates, used in food packagings, medical products, cosmetics and children toys; Triethyl citrate (TEC); Acetyl triethyl citrate (ATEC), higher boiling point and lower volatility than TEC; Tributyl citrate (TBC); Acetyl tributyl citrate (ATBC), compatible with PVC and vinyl chloride copolymers; Trioctyl citrate (TOC), also used for gums and controlled release medicines; Acetyl trioctyl citrate (ATOC), also used for printing ink; Trihexyl citrate (THC), compatible with PVC, also used for controlled release medicines; Acetyl trihexyl citrate (ATHC), compatible with PVC; Butyryl trihexyl citrate (BTHC, trihexyl o-butyryl citrate), compatible with PVC; Trimethyl citrate (TMC), compatible with PVC; alkyl sulphonic acid phenyl ester, polyethylene glycol (PEG) or any combination thereof. Optionally, the plasticizer can comprise triethyl citrate NF/EP.

In embodiments, the above-mentioned immediate-release and/or delayed release compositions comprises: a filler or binder, a disintegrating or dissolution promoting agent, a lubricant, a silica flow conditioner and a stabilizing agent. In an embodiment, the filler or binder is microcrystalline cellulose. In an embodiment, the disintegrating or dissolution promoting agent is sodium croscarmellose. In an embodiment, the lubricant is magnesium stearate. In an embodiment, the silica flow conditioner is silicon dioxide. In an embodiment, the stabilizing agent is magnesium trisilicate.

Methods and Agents to Effect Delayed Release

Delayed release can be effected by the use of one or more release-delaying agents. Any combination of release-delaying agents, including the ones described herein, can be used in the dosage forms. The release-delaying agent acts to increase the period before release begins from a dosage form. The length of the lag period before delayed release occurs can by controlled using methods known to those of skill in the art, for instance by varying the choice, combination, form, shape and/or amount of release-delaying agent(s).

The delayed release formulations can be prepared, for example, by coating active ingredients or an active ingredient-containing composition with one or more release-delaying agents. In other instances, the release-delaying agent(s) can be intermixed with or in co-solution with the active ingredients. For example, delayed release by osmotic rupture can be achieved by a dosage form comprising one or more swelling agents that are contained in combination with the active ingredients within a semipermeable coating. The increase in volume of the swelling agent upon exposure of the unit dosage form to bodily fluids causes the semipermeable coating to rupture. In such agents, both the swelling agent and the semipermeable coating can be considered to be release-delaying agents. Thus, delayed release can be achieved by a combination of release-delaying agents, where each release-delaying agent does not necessarily delay release by itself.

Delayed release can be achieved by various processes such as dissolution, diffusion, erosion (e.g., based on the inherent dissolution of the agent and incorporated excipients), and/or rupture (e.g., by swelling). Common mechanisms include bulk erosion of polymers which restrict diffusion of the drug, surface erosion, (e.g., of layered medicaments), or rupture. Rupture can be osmotically controlled, for instance by swelling that results from the osmotic infusion of moisture. Rupture can also result from the reaction of effervescent agents, e.g., citric acid/sodium bicarbonate, with water or other fluids that penetrate into the dosage form. Release, including delayed release, from a unit dosage form can be achieved by more than one mechanism. For example, release can occur for example by simultaneous swelling and diffusion, simultaneous diffusion and erosion, and simultaneous swelling, diffusion and erosion.

Methods of making delayed-burst release formulations are within ordinary skill. Examples are presented herein and can also be found in numerous publications, including U.S. Pat. Nos. 4,865,849, 4,871,549, 4,897,270, 5,017,381, 5,110,597, 5,260,068, 5,260,069, 5,387,421, 5,472,708, 5,508,040, 5,593,697, 5,840,329, 6,500,457, 6,531,152, 6,555,136, 6,627,223, 6,632,451 and 7,048,945.

Alternatively, delayed release can be initiated by a triggering signal such as a fluctuation in temperature, or an electromagnetic pulse. See, e.g., US Patent Publication Nos. 2001/6251365, 2006/997863, 2003/6514481, 2006/0057737, 2006/0178655, 2006/0121486, and 2006/0100608.

Two common classes of release-delaying agents are "enteric" (allowing release within a specific milieu of the gastro-intestinal tract) and "fixed-time" (allowing release after a "predetermined" or "fixed" time period after administration, regardless of gastro-intestinal milieu), each of which is discussed in more detail below. Enteric release-delaying agents for instance allow release at certain pHs or in the presence of degradative enzymes that are characteristically present in specific locations of the GI tract where release is desired. The unit dosage forms can comprise more than one release-delaying agent from any class, such as a combination of enteric and fixed-time release-delaying agents. In another embodiment, the release-delaying agent allows the release of drug after a predetermined period after the composition is brought into contact with body fluids ("fixed-time delayed release"). Unlike enteric release, fixed-time release is not particularly affected by environmental pH or enzymes.

A large number of fixed-time release-delaying agents are known to those of ordinary skill in the art. Exemplary materials which are useful for making the time-release coating of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose, cellulose acetate, cellulose acetate butyrate and ethyl cellulose; and other materials known to those of ordinary skill in the art. Other film-forming materials that can be used for this purpose include poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer. Other materials which can be used in the time-release coating include Acryl-EZE®, Eudragit® NE, RL and RS, hydroxypropylcellulose, microcrystalline cellulose (MCC, Avicel™ from FMC Corp.), poly (ethylene-vinyl acetate) (60:40) copolymer (EVAC from Aldrich Chemical Co.), 2-hydroxyethylmethacrylate (HEMA), MMA, and calcium pectinate can be included. Substances that are used as excipients within the pharmaceutical industry can also act as release-delaying agents.

Common types of fixed-time release dosage forms include erodible formulations, formulations that undergo osmotic rupture, or unit dosage form that use any combination of mechanisms for delayed release.

Fixed-time release-delaying agents can optionally achieve a delayed-burst release by osmotic rupture. Examples of such RDAs include swelling agents, osmogens, binders, lubricants, film formers, pore formers, coating polymers and/or plasticizers.

Osmotic rupture is achieved by a delayed release component which comprises a coated unit dosage form that contains the drug and a swelling agent within the semipermeable coating (e.g., ethylcellulose). The coating weight (thickness) of the semipermeable coating can be selected to delay release by osmotic rupture for a desired period. To identify the correct coating weight for a particular delay, unit dosage forms with a range of coating weights can be tested via in vitro dissolution to determine the burst time. Based on these results, a coating weight that achieves the desired lag period would be selected. In addition, the amount and/or ratio of a coating strength modifier (e.g., talc) in the coating can be adjusted as well. Other formulation variables that can also be adjusted to obtain the desired release by osmotic rupture include the amount of sweller layer and sweller and/or fillers in the formulation. In the case of rupturing tablets, the amount of sweller would be selected to achieve the target release, while still providing the tablet with sufficient compressibility and acceptably low friability to be manufacturable.

In an embodiment, the unit dosage form can comprise one or more "diffusion regulators" that control the permeation of bodily fluids into the drug-containing core. Exemplary diffusion regulators include hydrophilic polymers, electrolytes, proteins, peptides, amino acids and others known to those of ordinary skill in the pharmaceutical sciences. In an example, the fixed-time release-delaying agent comprises a coating that permits release of the active ingredients after a fixed period. The thickness of the coating can affect the time required for penetration of fluids into the formulation. For example and without limitation, a diffusion controlling time release coating that provides release after a fixed delay period of about 0.5-2.5 hours could be about 200-1000 microns thick, and one that provides a release after a fixed delay period of about 2.5-5.0 hours could be about 1000-3000 microns thick.

Erodible formulations provide another example of fixed-time release formulations. The release delay from an erodible coated tablet can be adjusted by those of ordinary skill in the art by regulating the erodible layer coating weight. To identify the correct coating weight, tablets over a range of coating weights can be tested via in vitro dissolution (and/or erosion) to determine the burst time. Other formulation variables that may affect performance include the selection of the coating layer polymer type and viscosity. In an embodiment, the unit dosage form can comprise one or more "erosion regulators" that control the erosion rate of the coating. Any material or combination of materials may serve as an erosion regulator. Exemplary erosion and/or diffusion regulators include hydrophilic polymers, electrolytes, proteins, peptides, amino acids and others known to those of ordinary skill in the pharmaceutical sciences. The thickness of the coating can affect the time required for erosion of the coating. For example and not limitation, an erodible time-release coating that provides release after a fixed period of about 0.5-2.5 hours could be about 100-2000 microns thick, and one that provides release after a fixed delay period of about 2.5-5.0 hours could be about 2000-5000 microns thick.

The release-delaying agent may comprise an "enteric" material that is designed to allow release upon exposure to a characteristic aspect of the gastrointestinal tract. In an embodiment, the enteric material is pH-sensitive and is affected by changes in pH encountered within the gastrointestinal tract (pH-sensitive release). The enteric material typically remains insoluble at gastric pH, then allows for release of the active ingredient in the higher pH environment of the downstream gastrointestinal tract (e.g., often the duodenum, or sometimes the colon). In another embodiment, the enteric material comprises enzymatically degradable polymers that are degraded by bacterial enzymes present in the lower gastrointestinal tract, particularly in the colon. Optionally, the unit dosage form is formulated with a pH-sensitive enteric material designed to result in a release within about 0-2 hours when at or above a specific pH. In various embodiments, the specific pH can for example be from about 4 to about 7, such as about 4.5, 5, 5.5, 6, 6.5 or 7.

Materials used for enteric release formulations, for example as coatings, are well known in the art and include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Acryl-EZE® (Colorcon, USA), Eudragit® (Rohm Pharma; Westerstadt, Germany), including Eudragit® L30D-55 and L100-55 (soluble at pH 5.5 and above), Eudragit® L-IOO (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylase and guar gum; zein and shellac. Combinations of different enteric materials may also be used. Multi-layer coatings using different polymers may also be applied. The properties, manufacture and design of enteric delivery systems are well known to those of ordinary skill in the art. See, e.g., Development of Biopharmaceutical Parenteral Dosage Forms (Drugs and the Pharmaceutical Sciences), by Bontempo (Publishers: Informa Healthcare (Jul. 25, 1997).

Those of ordinary skill in the art can adjust the period before delayed release from enteric coated multiparticulates by varying the enteric layer coating weight and composition. For example, where time in the stomach is <4 hours and some amount of protection (1-3 hours) is desired after the dosage form leaves the stomach, then an appropriate level of coating that provides up to 4 hours of protection between administration and drug release can be prepared.

Unit Dosage Forms

Monolithic Dosage Forms. In an embodiment, the unit dosage form is monolithic in nature, e.g., in the form of a tablet or capsule or a caplet (capsule-form tablet). Monolithic unit dosage forms may vary in shape and may be, for example, round, ovoid, oblong, cylindrical (e.g., disk shaped) or any other geometric shape, for example rectilinear. For example, the unit dosage form can have a disk or ovoid shape, or a shape like a flattened disk or torpedo. The edges can be beveled or rounded. The unit dosage form itself comprises two or three separate subunits, e.g., two compositions, one designed for immediate release of the active ingredients, and the second composition designed for delayed release of the active ingredients. The unit dosage form can be provided in certain embodiments (e.g., non-monolithic embodiments) as a kit comprising separate components.

Multiparticulate Forms. Although the unit dosage form may be a monolithic entity, the active ingredients contained within the unit dosage form need not be in monolithic form. For instance, one or more active ingredients can be multiparticulate in form. Active ingredients in multiparticulate form for example comprise a plurality of drug-containing beads, particles or granules. Such multiparticulate forms are for instance incorporated into a unit dosage form that is a tablet or capsule.

Tablet/Capsule Combinations of Formulations—Coated Core Tablets. One or more active ingredients can be present in the form of a tablet or capsule within the unit dosage form. Active ingredients in tablet form can be incorporated into a unit dosage form that is a capsule. Alternatively, tablet-type active ingredients can be used as an inner core in a "coated core" tablet-type unit dosage form. In one such example, the unit dosage form comprises a multilayered tablet, with an inner core of active ingredients for delayed release, and one or more outer layers that comprise active ingredients for immediate release. In an embodiment, a unit dosage form comprising an enteric-coated tablet to provide the delayed release, contained within a larger tablet that contains the immediate release formulation.

Tablet Delayed Release in Capsule Dosage Form. In another example, the delayed release component is in the form of a tablet or capsule, while the immediate release component is in the form of a flowable powder. The active ingredients may be formulated independently or in combination. The final unit dosage form can be in the form of a capsule, and in such cases the delayed release component can be sized and shaped so as to be easily accommodated within the capsule, while allowing for inclusion of the immediate release component as well. As understood by those skilled in the art, the tablet or capsule configuration of the delayed release formulation may be specifically sized and shaped for such a purpose. Upon administration, the unit dosage form capsule releases the immediate release active ingredients present in the flowable powder(s), and the delayed release tablet or capsule releases active ingredients at a later timepoint.

In an embodiment, the unit dosage form can include more than one discrete and separable formulation, wherein each formulation comprises at least one active ingredient of the unit dosage form. In such instances, the formulations can be separately prepared, and then combined into the final unit dosage form. In another embodiment, the active ingredient can be coformulated such that they are physically inseparable. In an embodiment, both (1) the doxylamine, analog thereof, derivative thereof, prodrug thereof, metabolite thereof and/or salt thereof, and (2) the pyridoxine, analog thereof, derivative thereof, prodrug thereof, metabolite thereof and/or salt thereof, immediate release formulations are powders, and the unit dosage form comprises a powder blend in which particles containing the doxylamine, analog thereof, derivative thereof, prodrug thereof, metabolite thereof and/or salt thereof are intermixed with particles containing the pyridoxine, analog thereof, derivative thereof, metabolite thereof, and/or salt thereof. In another embodiment, a co-solution of (1) the doxylamine, analog thereof, derivative thereof, prodrug thereof, metabolite thereof and/or salt thereof, and (2) the pyridoxine, analog thereof, derivative thereof, prodrug thereof, metabolite thereof and/or salt thereof, is processed, e.g., by spray-drying or lyophilization, into an immediate release powder, wherein both (1) the doxylamine, analog thereof, derivative thereof, prodrug thereof, metabolite thereof and/or salt thereof, and (2) the pyridoxine, analog thereof, derivative thereof, prodrug thereof, metabolite thereof and/or salt thereof, can be found together within a single particle of the powder. Optionally the (1) the doxylamine, analog thereof, derivative thereof, prodrug thereof, metabolite thereof and/or salt thereof, and (2) the pyridoxine, analog thereof, derivative thereof, prodrug thereof, metabolite thereof and/or salt thereof, can be in solid solution within such particles, and/or form a single continuous phase.

In an embodiment, the immediate release composition and the delayed release composition are comprised in the dual release oral dosage form in a layered arrangement with respect to one another. In another embodiment, the immediate release composition and the delayed release composition are comprised in the dual release oral dosage form adjacent to one another.

In an embodiment, the dual release oral dosage form comprises (a) a core comprising said delayed release composition and (b) one or more coats substantially surrounding the core, said one or more coats comprising the immediate release composition.

In an embodiment, the dual release oral dosage form comprises (a) delayed release granules or microspheres comprising the delayed release composition and (b) immediate release granules or microspheres comprising the immediate release composition.

In an embodiment, the immediate release composition is in contact with the delayed release composition, within said dual release oral dosage form. In another embodiment, the immediate release composition is not in contact with (i.e., spaced away from) the delayed release composition, within said dual release oral dosage form.

Manufacture of Dosage Forms

The active ingredients may conveniently be presented in unit dosage form and may be prepared by any of the methods well known in the art of pharmacy. Techniques and formulations generally are found in for example Remington's Pharmaceutical Sciences (Mack Publishing Co., Easton, Pa.). Such methods include the step of bringing into association of one or more active ingredients with any additional excipients. In general, the dosage forms are prepared by uniformly and intimately bringing into association the active ingredients with liquid carriers or finely divided solid carriers or both, and then, if necessary, shaping the product or filling capsules.

In an embodiment, the unit dosage form and/or one or more formulations are in tablet form. Various methods of preparation of tablets are well known to one of ordinary skill in the art. See, e.g., Pharmaceutical Dosage Forms: Tablets, Third Edition, by Larry L. Augsburger and Stephen W. Hoag (publisher: Informa Healthcare; Dec. 15, 2007). These methods include direct compression and granulation (e.g., wet or dry or fluid-bed).

The pellets can be made by, for example, simple granulation such as wet granulation or dry granulation, followed by sieving; extrusion and marumerization (spheronization); rotogranulation; or any agglomeration process that results in a pellet of reasonable size and robustness. For extrusion and marumerization, the drug and other additives are granulated by addition of a binder solution. The wet mass is passed through an extruder equipped with a certain size screen, and the extrudates are spheronized in a marumerizer. The resulting pellets are dried and sieved for further applications. One may also use high-shear granulation, wherein the drug and other additives are dry-mixed and then the mixture is wetted by addition of a binder solution in a high shear-granulator/mixer. The granules are kneaded after wetting by the combined actions of mixing and milling. The resulting granules or pellets are dried and sieved for further applications. Alternatively, the immediate release beadlets or pellets are prepared by solution or suspension layering, whereby a solution or dispersion of the active ingredients, with or without a binder and optionally an anti-tacking agent such as talc, is sprayed onto a core or starting seed (either prepared or a commercially available product) in a fluid bed processor or other suitable equipment. The cores or starting seeds can be, for example, sugar spheres or spheres made from microcrystalline cellulose. The active ingredients, thus, are coated on the surface of the starting seeds. The active ingredients may also be layered onto the active ingredients-containing pellets described above, if desired. Following, drug layering, the resulting active ingredients-loaded pellets are dried for further applications. A protective layer, or overcoating, may be desired to ensure that the active ingredients-loaded pellets do not aggregate during processing or upon storage. The protective coating layer may be applied immediately outside the core, either an active ingredients-containing core or an active ingredients-layered core, by conventional coating techniques such as pan coating or fluid bed coating using solutions of polymers in water or suitable organic solvents or by using aqueous polymer dispersions. OPADRY®, OPADRY II® (Colorcon) and corresponding color and colorless grades from Colorcon can be used to protect the pellets from being tacky and provide colors to the product. Different anhydride-based polymers (e.g., sebacic/fumaric copolymers such as Spheromer™ I or Spheromer™ II from Spherics, Inc.) may also be used as protective layer. In certain embodiments, many ingredients can be incorporated into the overcoating formula, for example to provide a quicker immediate release, such as plasticizers: acetyltriethyl citrate, triethyl citrate, acetyltributyl citrate; dibutylsebacate, triacetin, polyethylene glycols, propylene glycol and the others; lubricants: talc, colloidal silica dioxide, magnesium stearate, calcium stearate, titanium dioxide, magnesium silicate, and the like.

In certain embodiments, the immediate release composition may be prepared as an uncoated tablet, or a tablet core prior to coating, comprising starch and a hydrophilic polymer acting as a matrix for a water-soluble drug or prodrug requires to have a certain minimum hardness in order to be able to resist breakage and/or attrition due to mechanical stresses imposed during a high-speed tableting operation (including all steps up to and including filling of the tablets into containers).

In yet other embodiments, the unit dosage form is in capsule form. Diverse capsule manufacturing and design methods are well known to one of ordinary skill in the art. See, e.g., Pharmaceutical Preformulation and Formulation: A Practical Guide from Candidate Drug Selection to Commercial Dosage Form, by Mark Gibson (publishers: Informa Healthcare, Aug. 1, 2001). When the unit dose form is a capsule, the method further comprises preparing the formulations into a form for loading and/or delivery, e.g., as a tablet, capsule and/or powder, and loading the formulations into the capsule to form the pharmaceutical unit dose.

Dosage

Dosage regimens may be adjusted to provide the optimum prophylactic/therapeutic response, via administration of a prophylactically or therapeutically effective amount of the active agent(s). A prophylactically or therapeutically effective amount is one in which any toxic or detrimental effects of the active agents (doxylamine, analog thereof, derivative thereof, prodrug thereof, metabolite thereof and/or salt thereof; and/or pyridoxine, analog thereof, derivative thereof, prodrug thereof, metabolite thereof and/or salt thereof) are outweighed by the prophylactic or therapeutic beneficial effects. For administration to a pregnant human female subject, the effective amount of the active agents is such that it is not toxic to the embryo or fetus.

In an embodiment, the dosage form comprises about 30 mg or less (e.g., about 25, 20, 15 mg or less) of the doxylamine, analog thereof, derivative thereof, prodrug thereof, metabolite thereof and/or salt thereof, in embodiments between about 5, 6, 7, 8, 9, 10, 11, 12, 13, 14, 15 to about 16, 17, 18, 19, 20, 21, 22, 23, 24, 25, 26, 27, 28, 29 or 30 mg. In an embodiment, the oral dosage form comprises about 5, 6, 7, 8, 9, 10, 11, 12, 13, 14, or 15 mg of the doxylamine, analog thereof, derivative thereof, prodrug thereof, metabolite thereof and/or salt thereof (e.g., doxylamine succinate). In an embodiment, the oral dosage form is adjusted so as to obtain a average plasma level of doxylamine from about 70 to about 250 ng/ml, in further embodiment from about 75 to about 235 ng/ml, from about 80 to about 200 ng/ml, from about 100 to about 160 ng/ml or from about 120 to about 140 ng/ml (e.g., about 125, 130, 135 or 140 ng/ml).

In an embodiment, the oral dosage form comprises about 80 mg or less (e.g., about 75, 70, 65, 60, 55, 50 mg or less) of the pyridoxine, analog thereof, derivative thereof, prodrug thereof, metabolite thereof and/or salt thereof, in embodiments between about 0.5, 1, 5, 10, 15, 20, 25, 30 mg to about 35, 40, 45, 50, 55, 60, 65, 70, 75 or 80 mg. In an embodiment, the dosage form comprises about 5, 6, 7, 8, 9, 10, 11, 12, 13, 14, 15, 16, 17, 18, 19, or 20 mg of the pyridoxine, analog thereof, derivative thereof, prodrug thereof, metabolite thereof and/or salt thereof (e.g., pyridoxine, PYL, PYP, PLP, PYM and/or PMP). In an embodiment, the dosage is adjusted so as to obtain an average plasma level of the pyridoxine, analog thereof, derivative thereof, prodrug thereof, metabolite thereof and/or salt thereof (e.g., PLP) from about 90 to about 160 ng/ml, in further embodiment from about 100 to about 150 ng/ml, from about 105 to about 145 ng/ml, or from about 110 to about 140 ng/ml (e.g., about 110, 115, 120, 125, 130, 135 or 140 ng/ml). In an embodiment, the dosage is adjusted so as to obtain an average $C_{max}$ of the pyridoxine, analog thereof, derivative thereof, prodrug thereof, metabolite thereof and/or salt thereof (e.g., PLP) from about 90 to about 160 ng/ml, in further embodiment from about 100 to about 150 ng/ml, from about 105 to about 145 ng/ml, or from about 110 to about 140 ng/ml (e.g., about 110, 115, 120, 125, 130, 135 or 140 ng/ml).

In an embodiment, the amount of the doxylamine, analog thereof, derivative thereof, prodrug thereof, metabolite thereof and/or salt thereof comprised in the immediate release component or composition is less than the amount of the doxylamine, analog thereof, derivative thereof, prodrug thereof, metabolite thereof and/or salt thereof comprised in the delayed release component or composition.

In another embodiment, the amount of the doxylamine, analog thereof, derivative thereof, prodrug thereof, metabolite thereof and/or salt thereof comprised in the immediate release component or composition is more than the amount of the doxylamine, analog thereof, derivative thereof, prodrug thereof, metabolite thereof and/or salt thereof comprised in the delayed release component or composition.

In another embodiment, the amount of the doxylamine, analog thereof, derivative thereof, prodrug thereof, metabolite thereof and/or salt thereof comprised in the immediate release component or composition is substantially equivalent to (i.e. the difference in the amounts is less than or equal to about 10, 9, 8, 7, 6, 5, 4, 3, 2, 1 or 0%) the amount of the doxylamine, analog thereof, derivative thereof, prodrug thereof, metabolite thereof and/or salt thereof comprised in the delayed release component or composition.

In an embodiment, the amount of the pyridoxine, analog thereof, derivative thereof, prodrug thereof, metabolite thereof and/or salt thereof comprised in the immediate release component or composition is less than the amount of the pyridoxine analog thereof, derivative thereof, prodrug thereof, metabolite thereof and/or salt thereof comprised in the delayed release component or composition.

In another embodiment, the amount of the pyridoxine, analog thereof, derivative thereof, prodrug thereof, metabolite thereof and/or salt thereof comprised in the immediate release component or composition is more than the amount of the pyridoxine, analog thereof, derivative thereof, prodrug thereof, metabolite thereof and/or salt thereof comprised in the delayed release component or composition.

In another embodiment, the amount of the pyridoxine, analog thereof, derivative thereof, prodrug thereof, metabolite thereof and/or salt thereof comprised in the immediate release component or composition is substantially equivalent to (i.e. the difference in the amounts is less than or equal to about 10, 9, 8, 7, 6, 5, 4, 3, 2, or 1%) the amount of the pyridoxine, analog thereof, derivative thereof, prodrug thereof, metabolite thereof and/or salt thereof comprised in the delayed release component or composition.

In an embodiment the ratio, by weight, of the amount of the doxylamine, analog thereof, derivative thereof, prodrug thereof, metabolite thereof and/or salt thereof comprised in the immediate release component or composition to the amount of the doxylamine, analog thereof, derivative thereof, prodrug thereof, metabolite thereof and/or salt thereof comprised in the delayed release component or composition is from about 5:0 about 0:5, in a further embodiment from about 4:0 to about 0:4, in a further embodiment from about 3:0 to about 0:3, in a further embodiment from about 2:0 to about 0:2, in a further embodiment from about 1.5:0 to about 0:1.5. In further embodiments, the ratio is from about 5:1 about 1:5, in a further embodiment from about 4:1 to about 1:4, in a further embodiment from about 3:1 to about 1:3, in a further embodiment from about 2:1 to about 1:2, in a further embodiment from about 1.5:1 to about 1:1.5.

In an embodiment the ratio, by weight, of the amount of the pyridoxine, salt thereof, metabolite thereof and/or salt of the metabolite comprised in the immediate release component or composition to the amount of the pyridoxine, salt thereof, metabolite thereof and/or salt of the metabolite comprised in the delayed release component or composition is from about 5:0 about 0:5, in a further embodiment from about 4:0 to about 0:4, in a further embodiment from about 3:0 to about 0:3, in a further embodiment from about 2:0 to about 0:2, in a further embodiment from about 1.5:0 to about 0:1.5. In further embodiments, the ratio is from about 5:1 about 1:5, in a further embodiment from about 4:1 to about 1:4, in a further embodiment from about 3:1 to about 1:3, in a further embodiment from about 2:1 to about 1:2, in a further embodiment from about 1.5:1 to about 1:1.5.

Treatment or Alleviation of the Symptoms of Nausea and Vomiting

In another aspect, the present invention provides a method for alleviating the symptoms of nausea and vomiting in a mammal, said method comprising administering an effective amount of the above-mentioned dual release oral dosage system or dual release oral dosage form to a mammal in need thereof.

In another aspect, the present invention provides a method for alleviating the symptoms of nausea and vomiting of human pregnancy (NVP), the method comprising administering an effective amount of the above-mentioned dual release oral dosage system or dual release oral dosage form to a pregnant human female in need thereof.

In another aspect, the present invention provides a use of the above-mentioned dual release oral dosage system or dual release oral dosage form for alleviating the symptoms of nausea and vomiting in a mammal.

In another aspect, the present invention provides a use of the above-mentioned dual release oral dosage system or dual release oral dosage form for alleviating the symptoms of NVP.

In another aspect, the present invention provides a use of the above-mentioned dual release oral dosage system or dual release oral dosage form for the preparation of a medicament for alleviating the symptoms of nausea and vomiting in a mammal.

In another aspect, the present invention provides a use of the above-mentioned dual release oral dosage system or dual release oral dosage form for the preparation of a medicament for alleviating the symptoms of NVP.

In another aspect, the present invention provides the above-mentioned dual release oral dosage system or dual release oral dosage form for use in alleviating the symptoms of nausea and vomiting in a mammal.

In another aspect, the present invention provides the above-mentioned dual release oral dosage system or dual release oral dosage form for use in the preparation of a medicament for alleviating the symptoms of NVP.

In another aspect, the present invention provides the above-mentioned dual release oral dosage system or dual release oral dosage form for use in the preparation of a medicament for alleviating the symptoms of nausea and vomiting in a mammal.

In another aspect, the present invention provides the above-mentioned dual release oral dosage system or dual release oral dosage form for use in alleviating the symptoms of NVP.

In an embodiment, the above-mentioned at least two dual release oral dosage forms are for administration from two to four times a day (i.e., within a 24 h period). In an embodiment, the administration is according to the following schedule: a first dual release oral dosage form in the evening (e.g., at about 10 PM), a second dual release oral dosage form in the morning (e.g., at about 8 AM) and a third dual release oral dosage form in the afternoon (e.g., at about 4 PM). In embodiments, the first, second and/or third dual release oral dosage forms may be identical or different. In an embodiment, the first, second and/or third dual release oral dosage forms are identical.

In another embodiment, the administration is according to the following schedule: a first dual release oral dosage form in the evening (e.g., at about 10 PM) and a second dual oral release dosage form in the morning (e.g., at about 10 AM). The first and second dual release oral dosage forms may be the same or different. In an embodiment, the first and second dual release oral dosage forms are identical.

In an embodiment, the above-mentioned at least two dual release oral dosage forms are for administration under fed (e.g., during a meal or less than 2 hrs before or after meal) or fasted conditions (e.g., at least 2 hrs before or after meal).

In another aspect, the present invention provides a kit for alleviating the symptoms of nausea and vomiting in a mammal, the kit comprising the above-mentioned dual release oral dosage system or dual release oral dosage form. In an embodiment, the kit further comprises instructions for using the dual release oral dosage system or dual release oral dosage form for alleviating the symptoms of nausea and vomiting in a mammal. The kit may further comprise one or more containers.

In another aspect, the present invention provides a kit for alleviating the symptoms of nausea and vomiting of human pregnancy (NVP), the kit comprising the above-mentioned dual release oral dosage system or dual release oral dosage form. In an embodiment, the kit further comprises instructions for using the dual release oral dosage system or dual release oral dosage form for alleviating the symptoms of NVP. The kit may further comprise one or more containers.

In an embodiment, the kit comprises at least two dual release oral dosage forms identified to be taken at different times of the day. For example, the kit may comprise a first dual release oral dosage form comprising an indicator (shape, color, markings, etc.) that it has to be taken at a certain time of the day (e.g., in the evening, e.g., at about 10 PM), and a second dual release oral dosage form comprising an indication (shape, color, markings, etc.) that it has to be taken at another time of the day (e.g., in the morning, e.g., at about 10 AM). At least two dual release oral dosage forms may be identical or different.

In another embodiment, the kit comprises instructions for using the dual release oral dosage system or dual release oral dosage form according to the following schedule: a first dual release oral dosage form in the evening (e.g., at about 10 PM) and a second dual release oral dosage form in the morning (e.g., at about 10 AM). The first and second dual release oral dosage forms may be the same or different. In an embodiment, the first and second dual release oral dosage forms are identical.

In an embodiment, the kit further comprises a container in which the above-mentioned dual release oral dosage system or dual release oral dosage form is packaged.

In an embodiment, the kit comprises a pharmaceutical dosage forms bearing a pregnancy-friendly indicia to graphically confirm the non-teratogenic aspect of said dosage form. Examples of such pregnancy-friendly indicia are described in PCT publication No. WO/2004/004694. In an embodiment, the indicia is the shape of a graphical illustration of a pregnant woman applied to the dosage form itself or to the container/package.

As used herein, the terms "subject" or "patient" are taken to mean warm blooded animals such as mammals, for example, cats, dogs, mice, guinea pigs, horses, bovine cows, sheep and humans. In an embodiment, the subject is a mammal, and more particularly a female. In a further embodiment, the above-mentioned subject is a human. In yet a further embodiment, the subject is a human female, and more particularly a pregnant human female.

MODES FOR CARRYING OUT THE INVENTION

The present invention is illustrated in further details by the following non-limiting examples.

Example 1

Non-linear Pharmacokinetics (PK)

The results depicted in FIG. 1 shows plasma level concentrations exhibit non-linear (i.e., do not change proportionally with dose) pharmacokinetics within the recommended Diclectin® dosage regimen. The dose vs. $C_{max}$ relationship demonstrates that the $C_{max}$ increases or decreases more than expected after increase of dose, based on a capacity limited metabolism as described by Michaelis-Menten kinetics. The human plasma concentration data ($C_{max}$) depicted in FIG. 1 also demonstrate complex non-linear, dose-dependent pharmacokinetics using pyridoxine and its metabolites. For pyridoxine, the $C_{max}$ increases less than expected, which could indicate either saturated plasma protein binding sites and/or auto-induction (when a drug increase its own rate of metabolism). For pyridoxal and PLP, which are known to be engaged in multiple biotransformation and enzymatic reactions, the data would indicate that under multi dose levels, the levels of these metabolites increase more than expected, again showing non-linear pharmacokinetics.

Example 2

Pharmacokinetics of Doxylamine, Pyridoxine and Pyridoxine Metabolites Under Various Conditions in Healthy Women The data depicted in FIGS. 2, 3A and 3B demonstrate that food reduces the concentration of doxylamine, pyridoxine and pyridoxal. Furthermore, the comparison of PK parameters after single dosage vs. multi dosage shows that there is a dose accumulation of pyridoxine and pyridoxine metabolites (FIG. 2, right column). The dose accumulation of doxylamine and of some of pyridoxine metabolites (notably PYL, PLP and PMP) is also demonstrated in FIG. 4. For example, there is a significant increase in $C_{max}$ and AUC, and a significant lengthening of $T_{1/2}$, for pyridoxal (FIG. 2). Finally, an analysis of various bioavailability studies shows that inter subject and inter study variations are significantly higher for pyridoxine relative to doxylamine (FIG. 5).

Thus, overall, the results show that pyridoxine, as a pro-drug, is rapidly metabolised and the amount thereof unchanged in blood is about 1%. With increasing dose, availability is not increased, indicative of saturation. Pyridoxal shows significant bioavailability increases at steady-state, much more than anticipated, and the kinetics do not show linearity. PLP appears to be the most available active metabolite and the one remaining in the systemic circulation the longest (FIG. 2). Food, time of dosing, multi dosage and enzyme capacity are some of the factors that impact the metabolism of pyridoxine and its metabolites.

Example 3

Pharmacokinetics of Doxylamine and PLP Under the Currently Recommended Diclectin® Dosage Regimen (2×10 mg at 10 pm, 10 mg at 8 am, and 10 mg at 4 pm)

Figure 6:
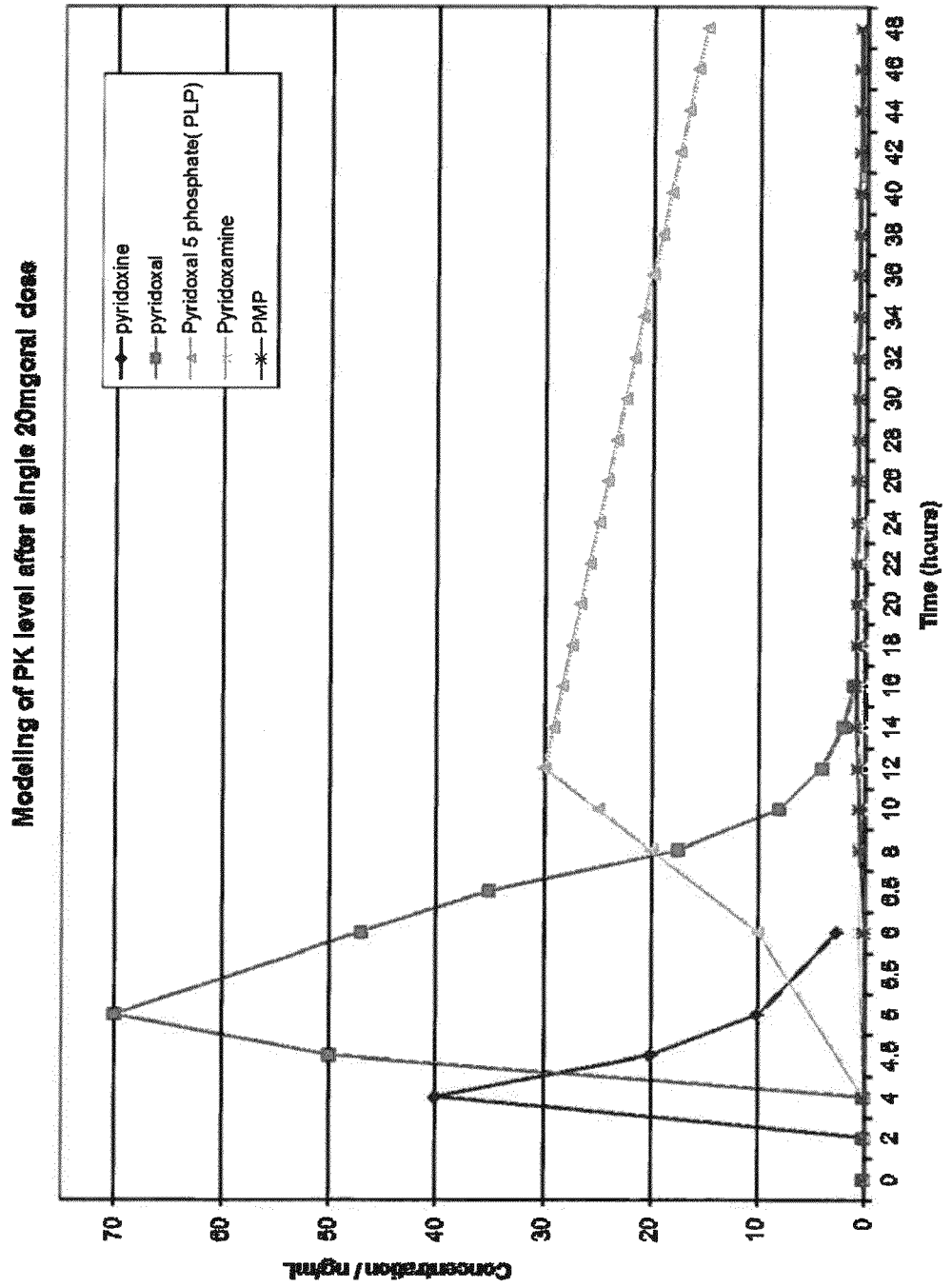
FIG. 6 shows the modeled plasma concentrations of pyridoxine and pyridoxine metabolites based on bioavailability studies of current formulation of Diclectin® (single 20 mg oral dose, 42 subjects)
Figure 7A:
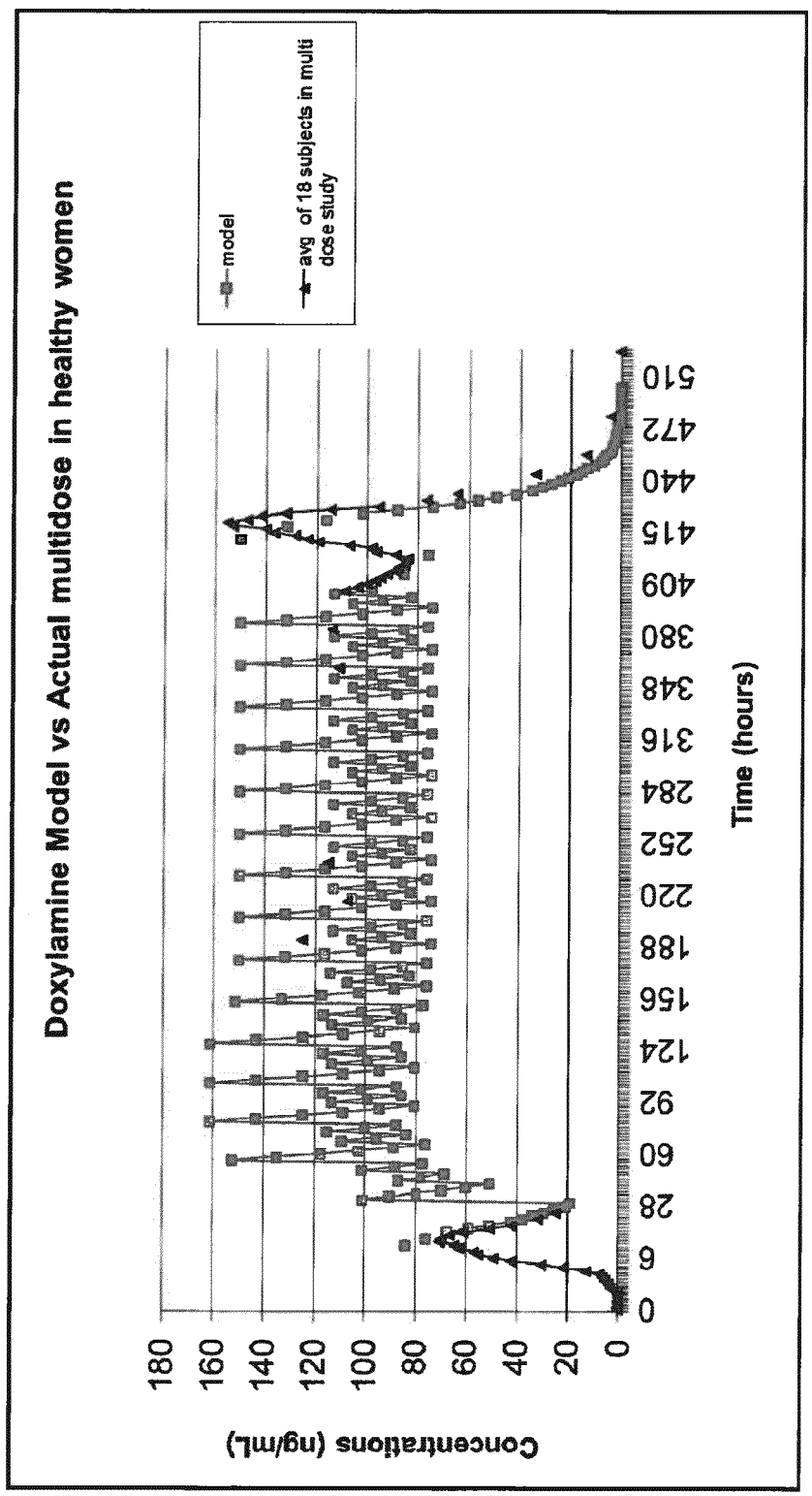
FIGS. 7A and 7B show the modeled (as determined by a simulation algorithm) and measured (multi dose steady state study) plasma concentrations of Doxylamine (FIG. 7A) and PLP (FIG. 7B) derived from bioavailability (BA) studies of Diclectin®.
Figure 7B:
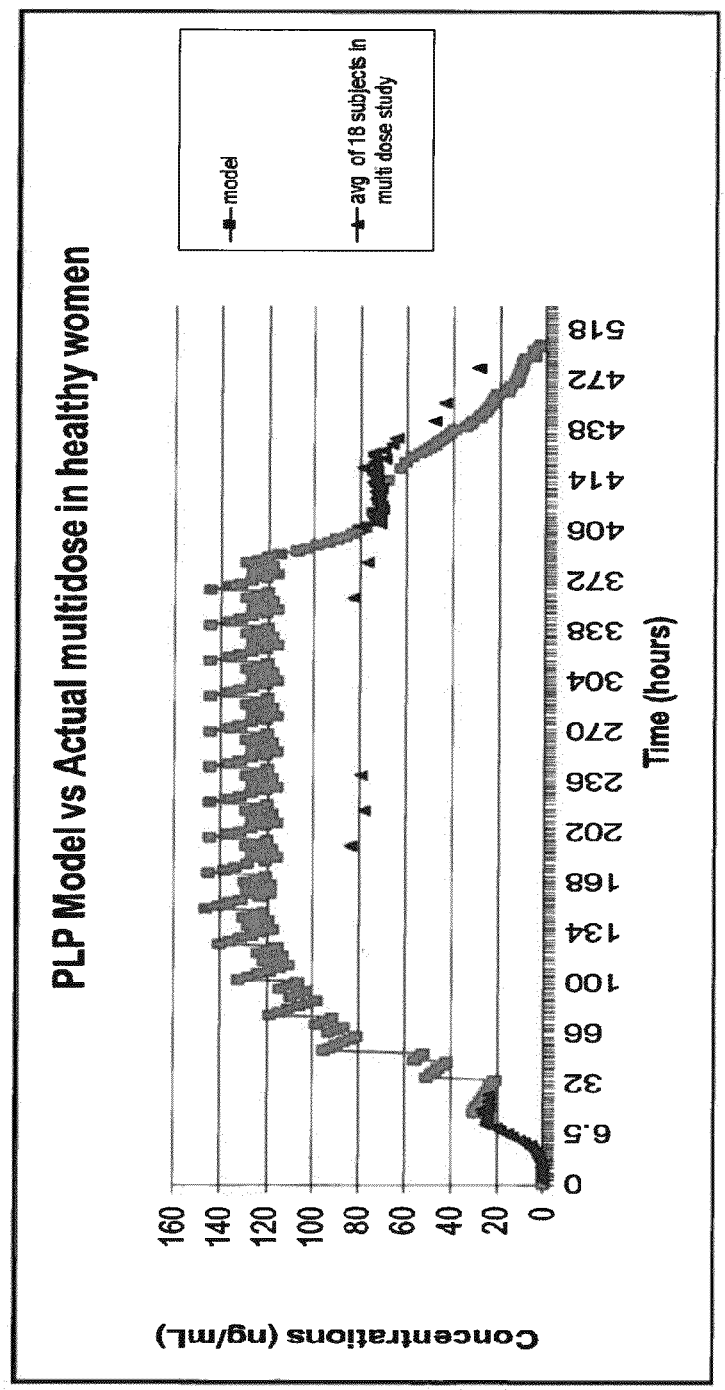

The data depicted in FIG. 6 shows that the kinetics of pyridoxine and its metabolites exhibit significant differences. PLP exhibits the highest systemic bioavailability, but on the other hand PLP also shows the longest time to appearance (FIG. 7A). The simulations were calculated based on pharmacokinetics data ($C_{max}$, $T_{max}$, $T_{1/2}$ and $K_{el}$) from bioavailability studies performed under fasted conditions in healthy women, following the method previously described in the art for non-linear elimination processes and the impact of saturable processes on kinetics of drug accumulation by Brocks D. and Mehvar R., "Rate and Extent of Drug Accumulation after Multiple Dosing Revisited", *Clin Pharmacokinet* 2010; 49(7):421-438. For doxylamine, the results from the multi-dose steady state study in healthy women are superimposable on the simulation algorithm. For PLP, the results from the multidose steady state study in healthy women match the simulation algorithm for the absorption and elimination phase (FIG. 7B). For distribution and metabolism, using data previously published in the art, the simulation algorithm calculated a corrected therapeutic concentration for pyridoxine and its metabolites to fit the data provided by the bioavailability studies performed under fasted conditions.

Figure 7C:
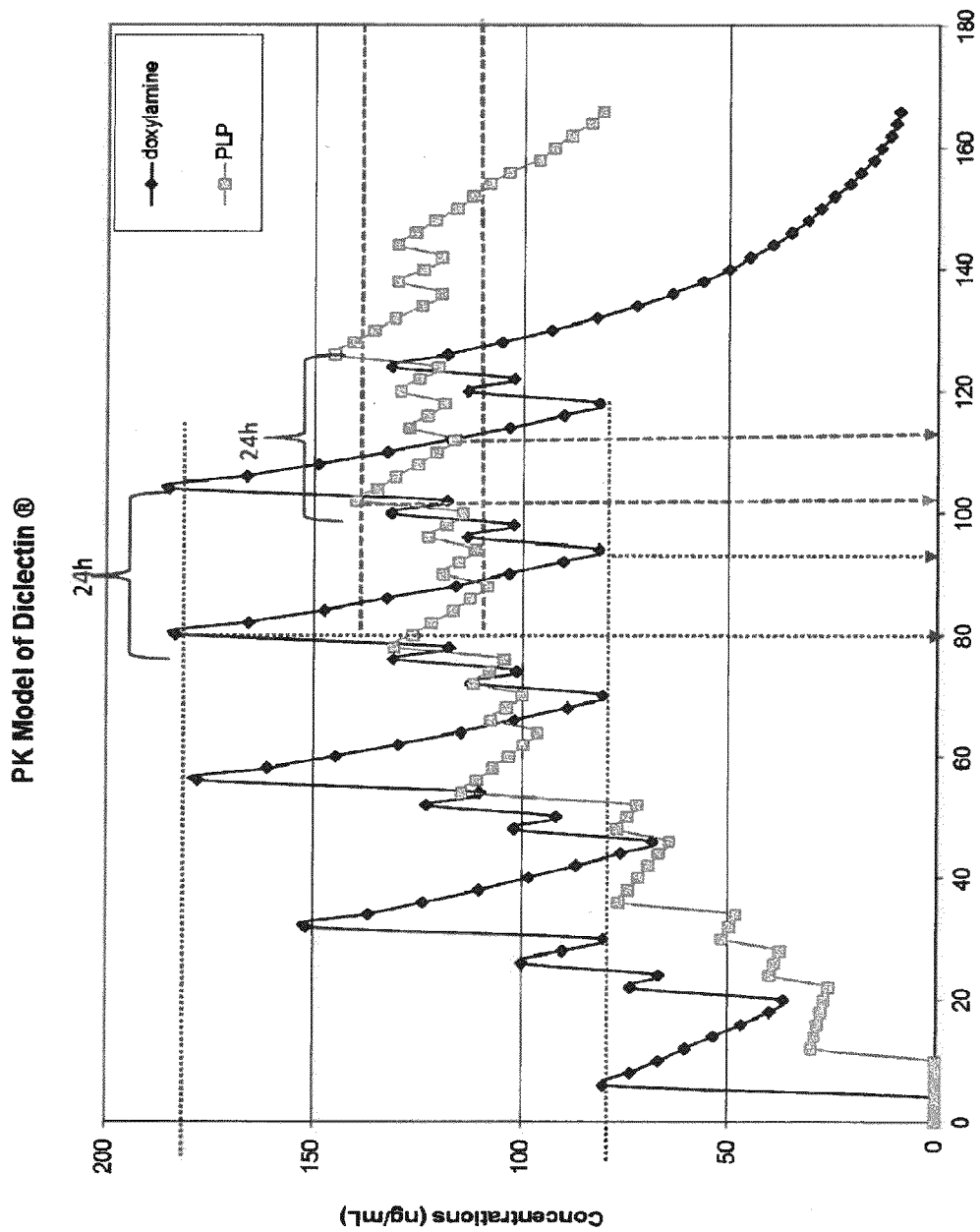
FIG. 7C shows the modeled (as determined by a simulation algorithm) plasma concentrations of Doxylamine and PLP, based on the currently used Diclectin® formulation.

As shown in FIG. 7C, for doxylamine, the average maximum level (180 ng/ml) is reached after about 82 h (3.4 days), and the minimum level (80 ng/ml) is maintained after about 96 hrs (4 days). For PLP, the maximum level (140 ng/ml) is reached after about 104 hrs (4 days), and the minimum level (120 ng/ml) is maintained after the same period. There is thus a difference of about 24 hrs between doxylamine and PLP to reach the maximum level, and the levels of Doxylamine decrease by more than half within the 24-hour delay, while PLP levels decrease only slightly.

The current formulation (Diclectin®) is highly suitable for the evening dose (20 mg at 10 PM), as the delayed release allows for a maximum level of doxylamine in the systemic circulation to be achieved at about 4 AM. By 8 AM, there are still relatively high levels in the systemic circulation, since the half-life of doxylamine is about 12 hrs. Thus, doxylamine taken as such around 10 PM is effective to act on morning NVP.

For pyridoxine (PYR), the maximum level is reached at about 2 AM for the evening dose, and it is converted into pyridoxal (PYL) by about 3 AM which is then converted to pyridoxal 5-phosphate level (PLP) to reach the maximum PLP concentration at about 9 AM. It is unlikely that PYR and PYL are the ingredients acting on morning NVP since that by 8 AM there is no more PYR in circulation due to fast half-life and negligible amounts of Pyridoxal. Therefore, PLP is believed to be the most active component against morning NVP, reaching a peak level at around 9 AM.

The morning (8 AM) dose (10 mg) when taken, reaches an average systemic maximum at about 2 PM for doxylamine and PLP levels would be maximum at around 8 PM. Furthermore the mid-afternoon (4 PM) dose (10 mg) would reach average maximum doxylamine levels at about 10 pm and average maximum PLP levels at about 4 AM. Therefore, the mid-afternoon (4 PM) dose is not significantly acting on daily NVP. Levels at steady state are reached only after 4 days, based on the half-life of doxylamine being 12 hrs and of PLP being 60 hrs based on the combined effect of dosing time, $T_{max}$ of delayed release, $t_{1/2}$, food and/or mutidosing.

The posology allows also for additional variation: Daily doses are not prescribed at specific times but rather morning and mid-afternoon. Furthermore it also suspected that the daytime doses may be taken with food or without, causing additional variation on kinetics and in turn impacting the effectiveness of reaching steady-state levels.

Example 4

Formulation NPD-101: Addition of an Immediate Release Core Containing 5 mg Pyridoxal to the Current Diclectin® Formulation (10 mg Doxylamine/10 mg Pyridoxine Rapid Onset, Delayed Released)

NPD-101 was designed to focus on the biotransformation intermediate components rather than on the parent (Pyridoxine) to yield higher and faster levels of the active moiety and to reduce variation in metabolism that is believed to contribute to the variation of effectiveness in patients. Pyridoxal is a metabolite that is an intermediate step between pyridoxine (Prodrug) and the PLP (active moiety), thus administering PYL instead of PYR saves one biotransformation step.

Figure 8:
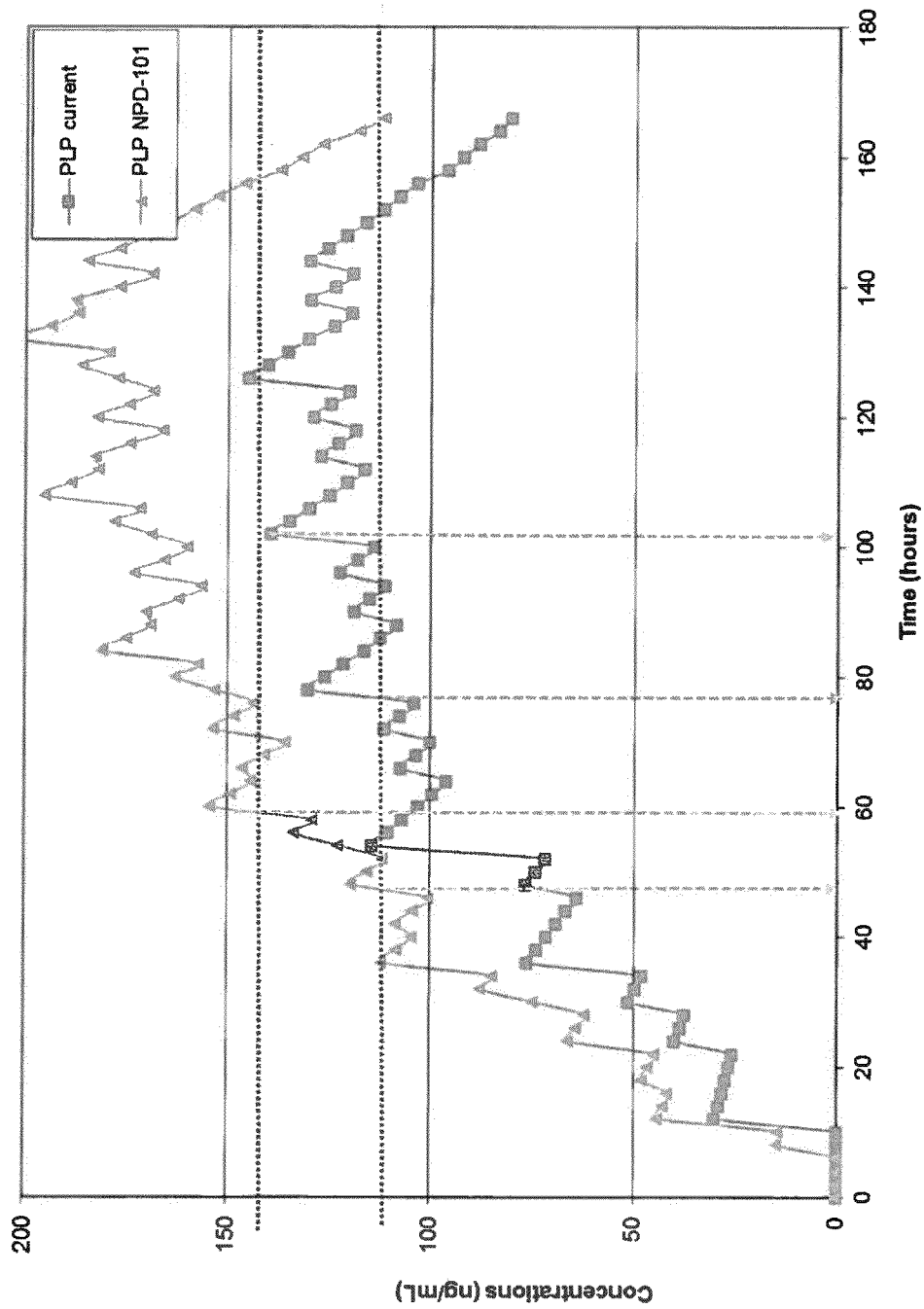
FIG. 8 shows a comparison of the modeled (as determined by a simulation algorithm) plasma concentrations of PLP between the currently used Diclectin® formulation (PLP) and formulation NPD-101 (PLP NPD-101)

The results of the PK simulation for NPD-101 are illustrated in FIG. 8. The calculated simulation therapeutic range of PLP is between 120 and 140 ng/ml, and NPD-101 would reach the lower therapeutic concentration range for PLP after about 45 hrs (vs. about 78 hrs for the current Diclectin® formulation) and maximum therapeutic levels after about 60 hrs (vs. about 100 hrs for the current Diclectin® formulation).

Pyridoxine maximum therapeutic levels are reached at about 2 AM, where it is converted into pyridoxal by about 3 AM, then converted to PLP to reach maximum PLP levels at about 9 AM. Adding pyridoxal as immediate release will result in PYL reaching peak levels at about 11 PM, and then converted to PLP for maximum PLP levels at about 5 AM, which is better timing to treat early morning NVP.

Addition of 5 mg of Pyridoxal in an immediate release core also allows the 8 AM dose to reach average maximal PLP levels at about 4 PM and then the 4 PM dose would reach average maximal PLP levels at about 10 PM, thus shortening the time to reach minimum steady state levels of PLP in about 36 hrs or 1.5 days.

Example 5

Formulation NPD-102: Addition of an Immediate Release Core Containing 5 mg Pyridoxal/5 mg Doxylamine to the Current Diclectin® Formulation Use of pyridoxal in the immediate release component would reduce the number of biotransformation steps to reach PLP as per NPD-101, and including doxylamine in the immediate release core provides a level of doxylamine sooner thereby reducing the gap between doses. The current Diclectin® formulation works very well for the evening dose (10 PM), the delayed release allowing a maximum level of doxylamine in the systemic circulation to be reached at about 4 AM in time to act for morning episodes of NVP. Adding 5 mg in an immediate release core allows the minimum estimated therapeutic level to be reached 8 hrs after the initial dose (instead of 24 hrs). For doxylamine, the 8 AM immediate release dose would reach maximum levels at 10 AM, and the 4 PM dose would reach maximum levels at 6 PM. The delayed release dose of 10 mg would reach maximum levels at about 5 AM, 6 PM and midnight (for the 10 PM, 8 PM and 4 PM doses, respectively) while the small 5 mg immediate release dose would reach peak at 2 AM, 10 AM and 8 PM (for the 10 PM, 8 AM and 4 PM doses, respectively). Also, the estimated maximum therapeutic level would be reached after 30 hrs instead of 58 hrs.

Figure 9:
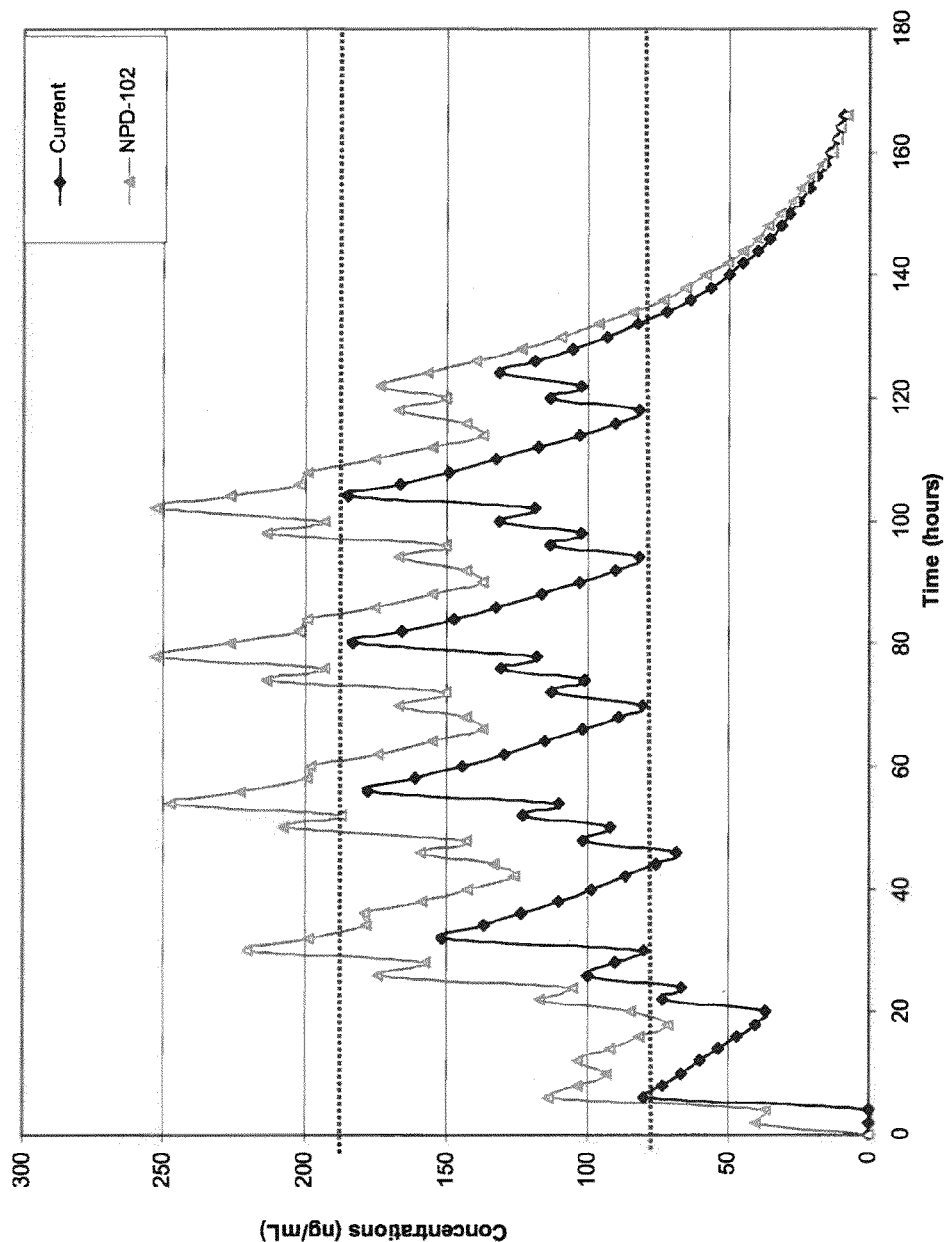
FIG. 9 shows a comparison of the modeled (as determined by a simulation algorithm) plasma concentrations of doxylamine between the currently used Diclectin® formulation (Current) and formulation NPD-102.

The therapeutic range is between 80 and 180 ng/ml, and doxylamine reaches average minimum levels within about 8 hrs (vs. about 24 hrs for the original Diclectin® formulation) and average maximum level after 30 hrs (vs. about 58 hrs for the current Diclectin® formulation), as depicted in FIG. 9. The profile for PLP is identical to that for NPD-101.

Example 6

NPD-102 at Different Dosage Regimens

Figure 10A:
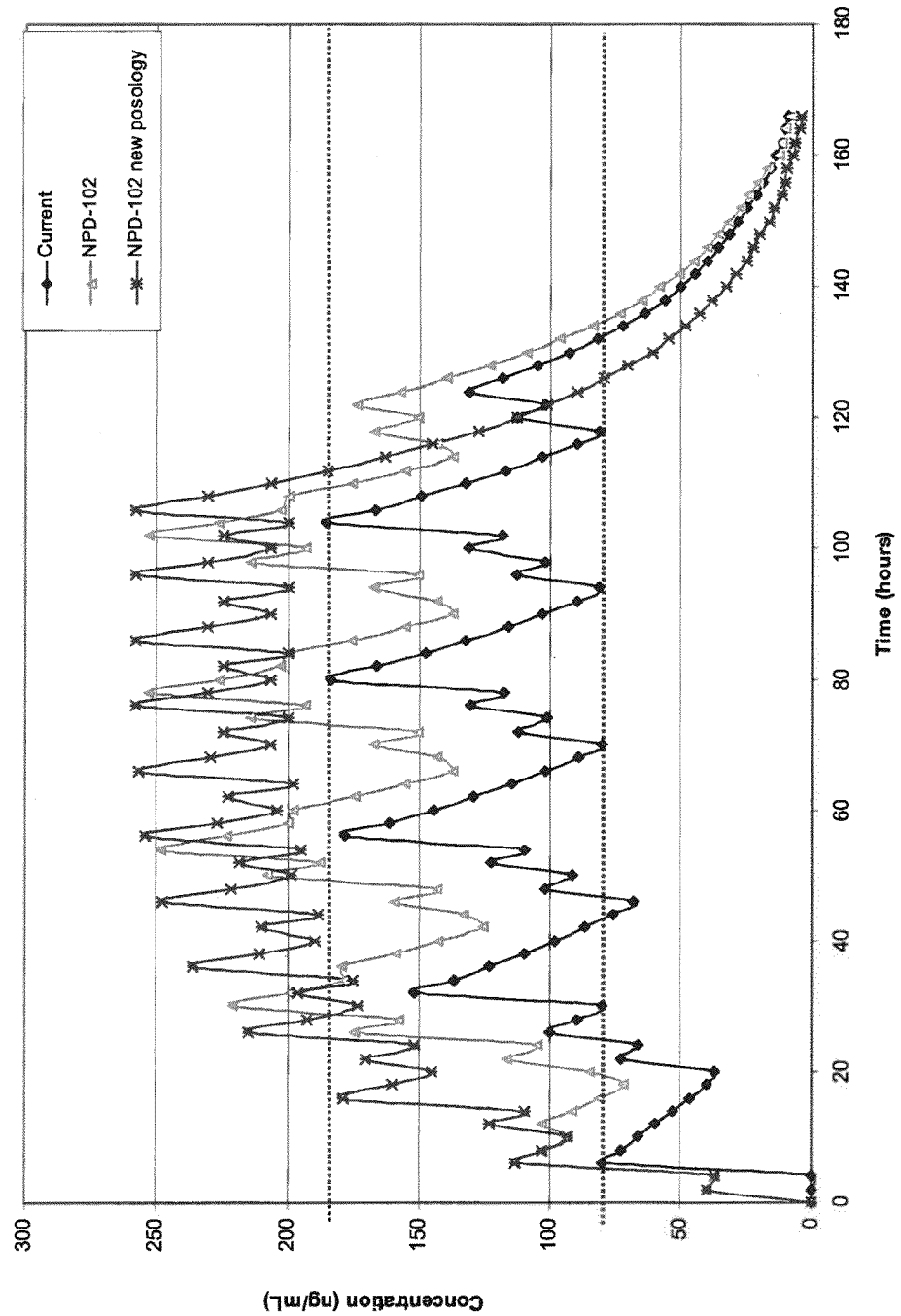
FIGS. 10A and 10B show a comparison of the modeled (as determined by a simulation algorithm) plasma concentrations of doxylamine (FIG. 10A) and PLP (FIG. 10B) between the currently used Diclectin® formulation, a first dosage regimen for NPD-102 (2 tablets at bedtime, 1 at 8 am and 1 at 4 pm); NPD-102 and a second dosage regimen for NPD-102 (2 tablets at 10 pm and 2 tablets at 10 am; NPD-102 new posology or 102 new posology)
Figure 10B:
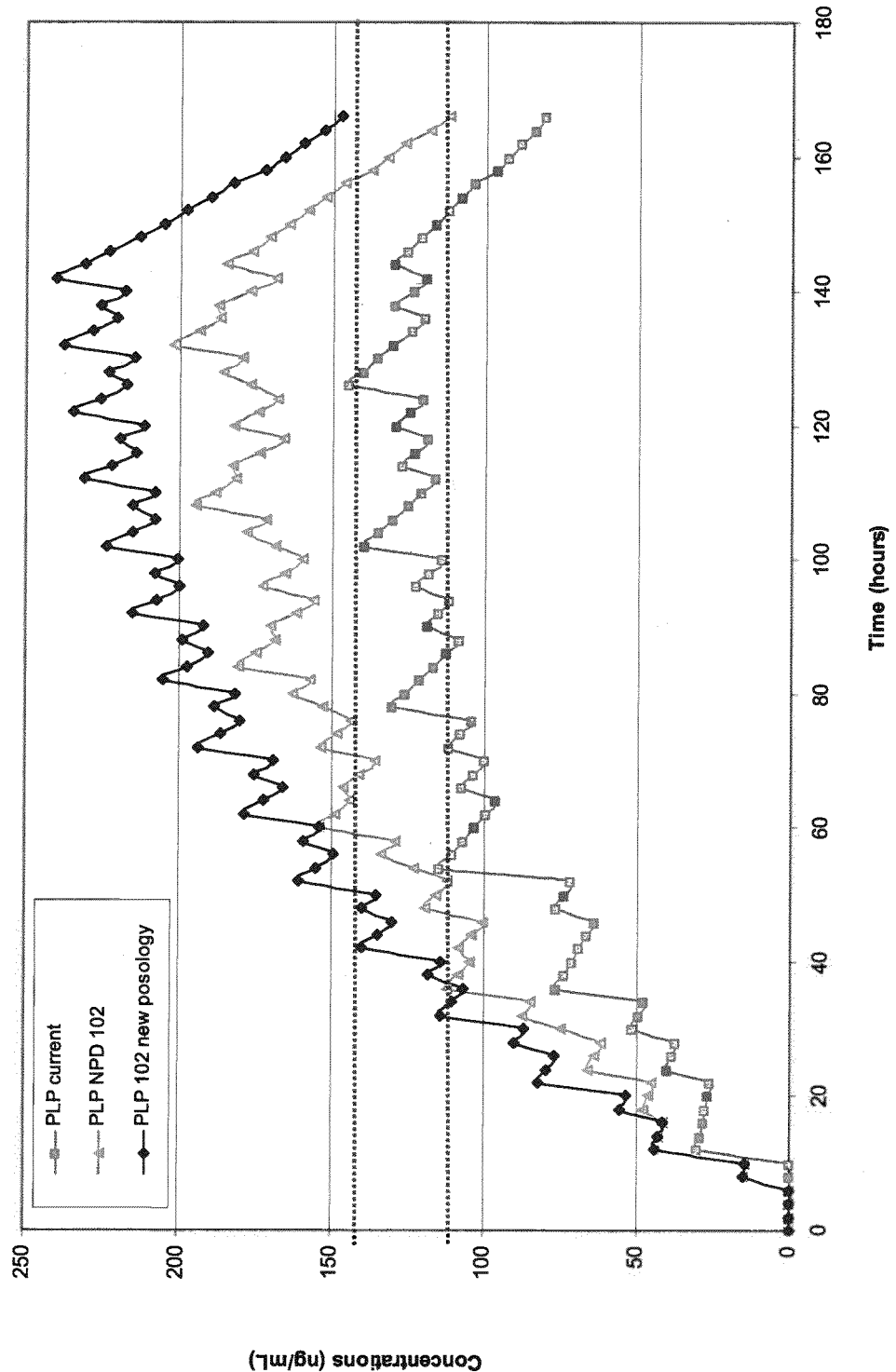

Two different dosage regimens were compared for NPD-102. The first regimen ("current" in FIGS. 10A and 10B) is identical to that currently used for the current Diclectin® formulation (2×10 mg at 10 PM, 10 mg at 8 AM and 10 mg at 4 PM), and the second one ("new posology" in FIGS. 10A and 10B) is as follows: 2×10 mg at 10 PM and 2×10 mg at 10 AM. The results of the PK simulation are depicted in FIG. 10A (for doxylamine) and 10B (for PLP). Dosage of 2×10 mg tablets twice per day (the second regimen) reduces time to reach plasma peak levels from 24 hrs to 10 hrs for doxylamine and from 36 to 20 hrs for PLP thereby significantly reducing variations in the concentration of doxylamine and PLP at steady state. As such, changing the dosing regimen would reduce the period or delay between peak plasma concentrations of doxylamine and PLP.

Example 7

Formulation NPD-105: 7.5 mg of Doxylamine and 7.5 mg of Pyridoxine in the Delayed-release Core and 2.5 mg of Doxylamine and 2.5 mg of Pyridoxal in the Immediate Release Core

In NPD-105, the total concentration of the active ingredients is maintained relative to the current Diclectin® formulation, but the total 10 mg of each active ingredient is divided between the immediate release core and the delayed release core.

Figure 11A:
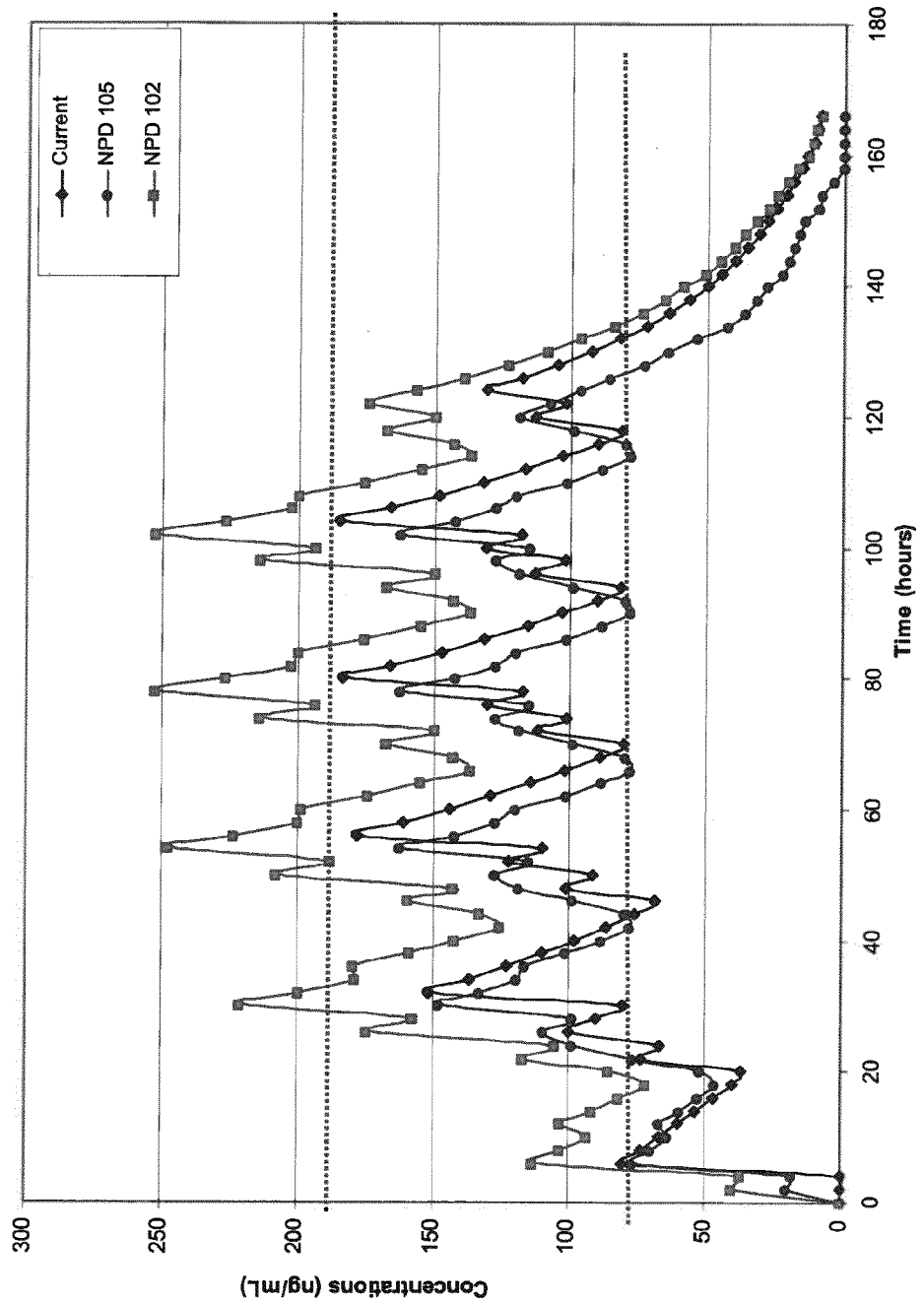
FIGS. 11A and 11B show a comparison of the modeled (as determined by a simulation algorithm) plasma concentrations of doxylamine (FIG. 11A) and PLP (FIG. 11B) between the currently used Diclectin® formulation (Current), formulation NPD-102 and formulation NPD-105.
Figure 11B:
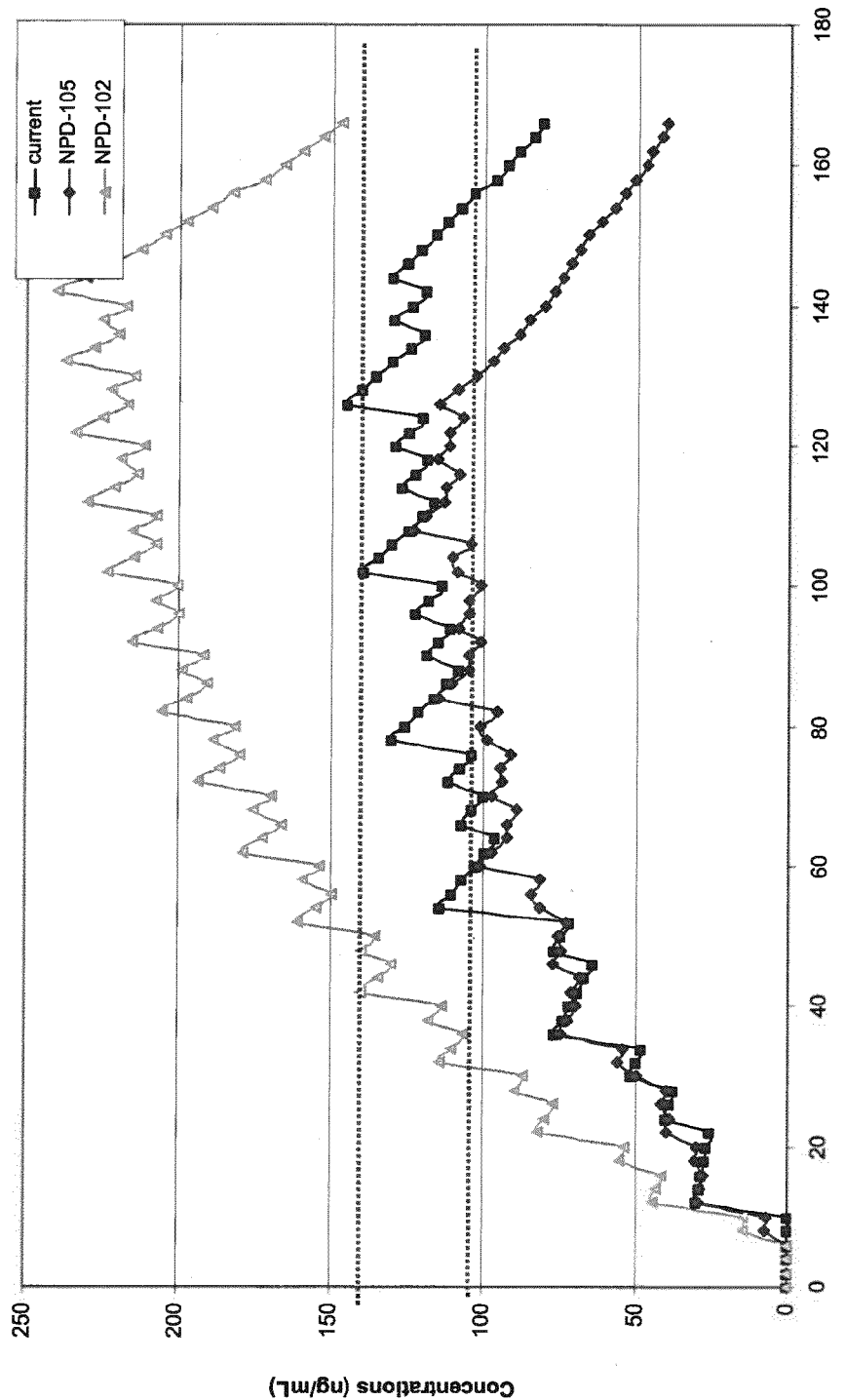
Figure 11C:
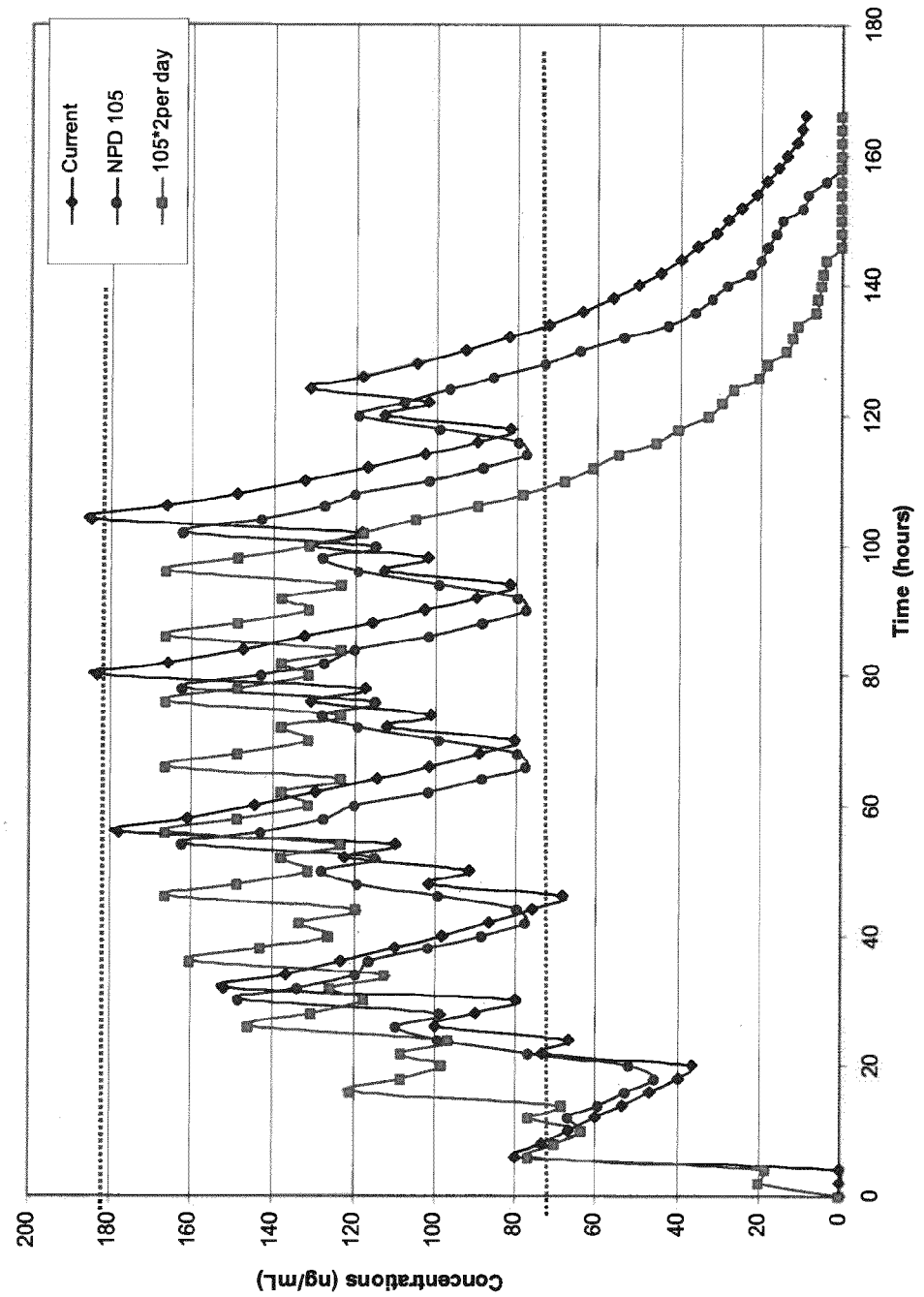
FIGS. 11C and 11D show a comparison of the expected (as measured by a simulation algorithm) plasma concentrations of doxylamine (FIG. 11C) and PLP (FIG. 11D) between the currently used Diclectin® formulation (Current), a first dosage regimen of formulation NPD-105 (2 tablets at bedtime, 1 at 8 am and 1 at 4 pm; NPD-105) and a second dosage regimen of formulation NPD-105 (2 tablets at 10 pm and 2 tablets at 10 am; 105*2 per day or NPD-105*2 per day)
Figure 11D:
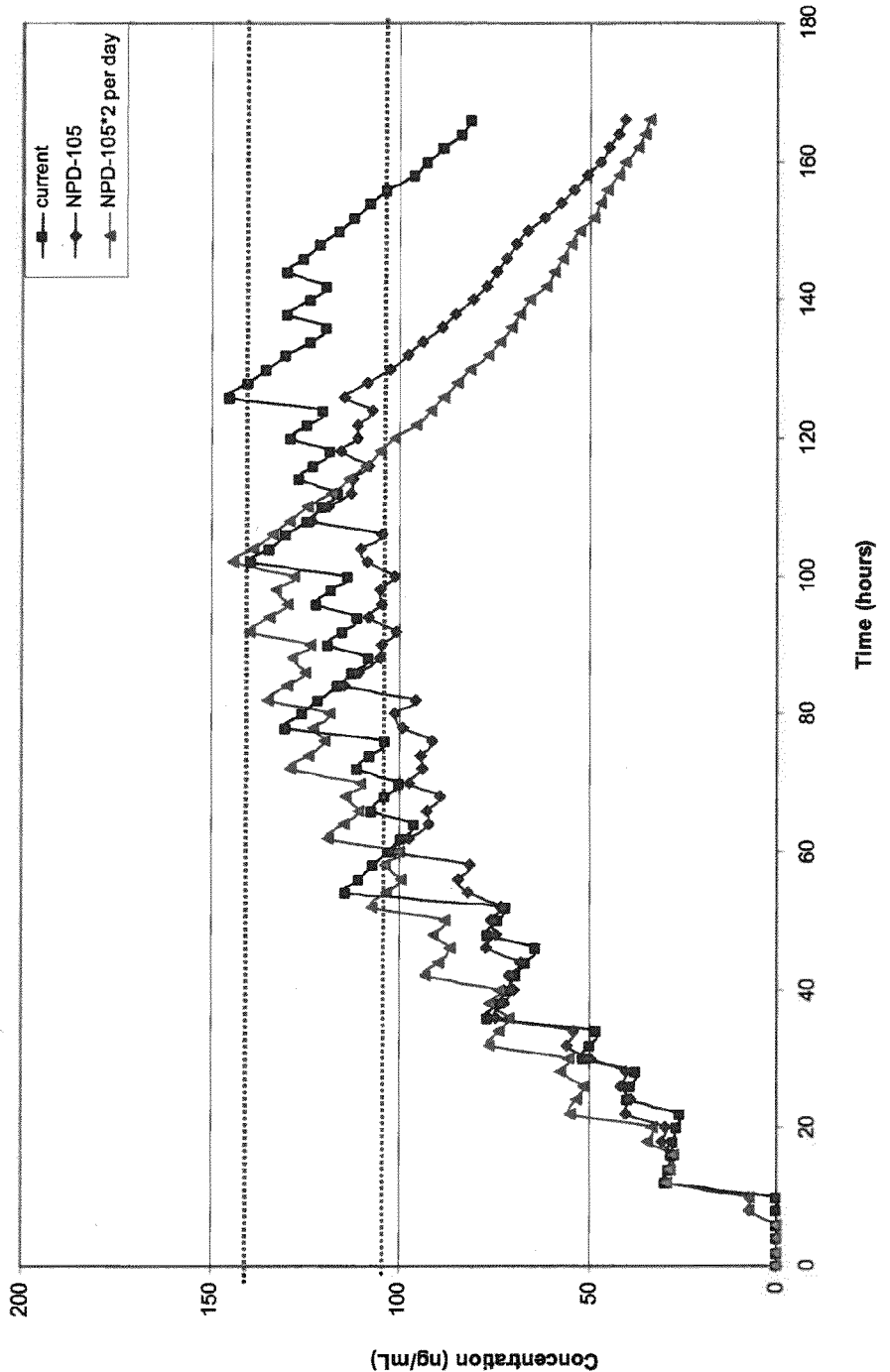

Since the therapeutic range of doxylamine is between 80 and 180 ng/ml, this formulation would remain in the estimated therapeutic range. The improvement in reaching the therapeutic levels for doxylamine and PLP are not as significant relative to formulation NPD-102 (FIGS. 11A and 11B). However, using the NPD-105 formulation under the "twice per day" dosing regimen (2×10 mg at 10 PM and 2×10 mg at 10 AM) would maintain the levels of doxylamine and PLP within the estimated therapeutic range and would reach this range faster as compared to the NPD-102 formulation (FIGS. 11C and 11D). Formulation NPD-105 taken "twice per day" may also attenuate the food effect and dose accumulation observed with the current formulation of Diclectin®.

Example 7

Comparison of Doxylamine and PLP Plasma Concentrations Following Administration of the Currently Used Diclectin® Formulation and of a New Formulation Comprising 10 mg/10 mg Doxylamine/Pyridoxine (Delayed Release)+10 mg/10 mg Doxylamine/Pyridoxal (Immediate Release)

Figure 12:
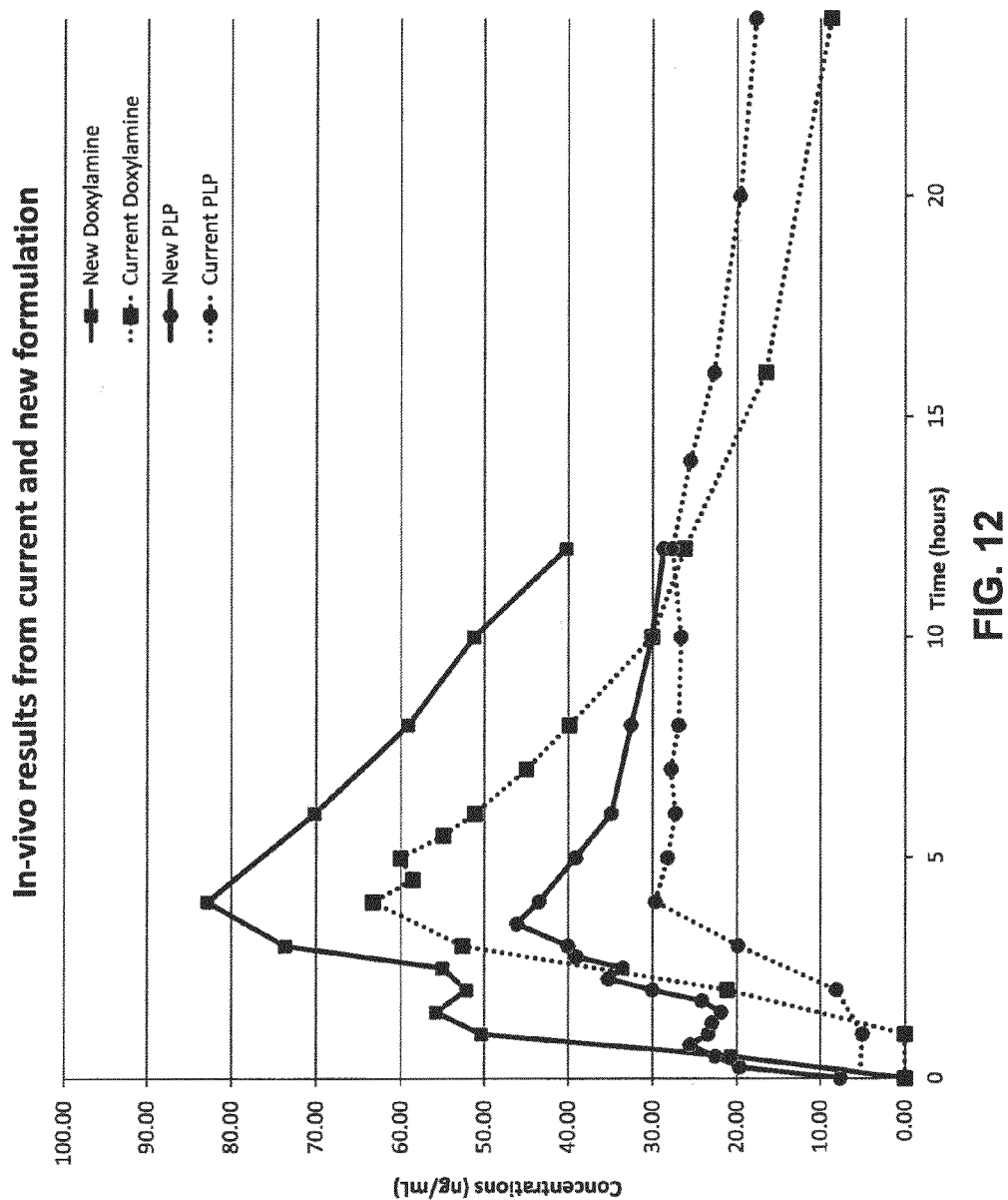
FIG. 12 shows the in vivo plasma concentrations of Doxylamine and PLP following administration of the currently used Diclectin® formulation (current Doxylamine/PLP) or of a new formulation comprising 10 mg/10 mg Doxylamine/Pyridoxine (Delayed Release)+10 mg/10 mg Doxylamine/Pyridoxal (Immediate Release).

The objective of this study was to determine the effect of an immediate release formulation containing doxylamine and a pyridoxine metabolite (pyridoxal) on the pharmacokinetics of pyridoxal-5'-phosphate, when co-administered with doxylamine succinate/pyridoxine-HCl 10 mg/10 mg delayed-release tablets (Diclectin®), under fasting conditions. Healthy female (n=12) participants between 18 and 45 years of age with a body mass index between 19 and 30 kg/m$^2$ were administered 2 tablets of Diclectin® or a combination of immediate (oral solution of 10 mg doxylamine succinate+10 mg pyridoxal-HCl from reconstituted powder) and delayed release under empty stomach conditions. Blood sampling was conducted extensively from 1 hour pre-administration until 24 hours post-administration. After a wash-out period of 21 days, dose administration and blood sampling was re-conducted as stated above. Doxylamine, and pyridoxine and its metabolites were measured using liquid chromatography-tandem mass spectrometry, as previously described (Nulman and Koren, *Can J Clin Pharmacol* Vol 16 (3):e400-e406, 2009). As shown in FIG. 12, administration of a combination of immediate (10 mg/10 mg Doxylamine/pyridoxal) and delayed (10 mg/10 mg Doxylamine succinate/Pyridoxine-HCl) release leads to a faster and higher increase in plasma levels of both Doxylamine and PLP, relative to administration of the currently used Diclectin® formulation.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms ° a", "an" and "the" include corresponding plural references unless the context clearly dictates otherwise.

What is claimed is:

1. A dual release oral dosage form comprising:
   (A) an immediate release composition comprising:
      (a) from about 5 mg to about 20 mg of doxylamine and/or a pharmaceutically acceptable salt thereof; and
      (b) from about 5 mg to about 20 mg of pyridoxine and/or a pharmaceutically acceptable salt thereof; and
   (B) a delayed release composition comprising:
      (a) from about 5 mg to about 20 mg of doxylamine and/or a pharmaceutically acceptable salt thereof; and
      (b) from about 5 mg to about 20 mg of pyridoxine and/or a pharmaceutically acceptable salt thereof;
   wherein said immediate release composition is for effecting release of (a) doxylamine and/or pharmaceutically acceptable salt thereof and (b) pyridoxine and/or pharmaceutically acceptable salt thereof, which begins prior to release of (a) doxylamine and/or pharmaceutically acceptable salt thereof and (b) pyridoxine and/or pharmaceutically acceptable salt thereof, from the delayed release component, within the gastrointestinal tract.

2. The dual release oral dosage form of claim 1, wherein said immediate release composition is for effecting release substantially within the stomach.

3. The dual release oral dosage form of claim 1, wherein said delayed release composition is for effecting release substantially within the intestine, and there is substantially no release from said delayed release composition in the stomach.

4. The dual release oral dosage form of claim 1, wherein said dosage form comprises from about 10 mg to about 20 mg of doxylamine and/or pharmaceutically acceptable salt thereof.

5. The dual release oral dosage form of claim 4, wherein said dosage form comprises about 20 mg of doxylamine and/or pharmaceutically acceptable salt thereof.

6. The dual release oral dosage form of claim 1, wherein said dosage form comprises from about 10 mg to about 25 mg of pyridoxine and/or pharmaceutically acceptable salt thereof.

7. The dual release oral dosage form of claim 6, wherein said dosage form comprises from about 10 mg to about 20 mg of pyridoxine and/or pharmaceutically acceptable salt thereof.

8. The dual release oral dosage form of claim 7, wherein said dosage form comprises about 20 mg of pyridoxine and/or pharmaceutically acceptable salt thereof.

9. The dual release oral dosage form of claim 1, wherein said dosage form comprises an identifying characteristic for correlation with its administration in a dosage regimen.

10. The dual release oral dosage form of claim 9, where said identifying characteristic is shape, color, an identifying mark, or any combination thereof.

11. The dual release oral dosage form of claim 1, wherein said dual release oral dosage form comprises (a) a core comprising said delayed release composition and (b) one or more coats substantially surrounding said core, said one or more coats comprising said immediate release composition.

12. The dual release oral dosage form of claim 11, wherein said core is coated with an enteric material.

13. The dual release oral dosage form of claim 1, wherein said immediate release composition is not in contact with said delayed release composition, within said dual release oral dosage form.

14. The dual release oral dosage form of claim 1, wherein said immediate release composition, delayed release composition, or both, further comprise at least one pharmaceutically acceptable carrier or excipient.

15. The dual release oral dosage form of claim 1, where said immediate release composition comprises a pharmaceutically acceptable doxylamine salt and a pharmaceutically acceptable pyridoxine salt.

16. The dual release oral dosage form of claim 1, wherein said delayed release composition comprises a pharmaceutically acceptable doxylamine salt and a pharmaceutically acceptable pyridoxine salt.

17. The dual release oral dosage form of claim 1, where said dual release oral dosage form is a tablet.

18. The dual release oral dosage form of claim 1, wherein the amount of doxylamine and/or pharmaceutically acceptable salt thereof comprised in the immediate release component or composition is substantially equivalent to the amount of doxylamine and/or pharmaceutically acceptable salt thereof comprised in the delayed release component or composition.

19. The dual release oral dosage form of claim 1, wherein the amount of pyridoxine and/or pharmaceutically acceptable salt thereof comprised in the immediate release component or composition is substantially equivalent to the amount of pyridoxine and/or pharmaceutically acceptable salt thereof comprised in the delayed release component or composition.

20. The dual release oral dosage form of claim 1, wherein said pharmaceutically acceptable doxylamine salt is doxylamine succinate.

21. The dual release oral dosage form of claim 1, wherein said pharmaceutically acceptable pyridoxine salt is pyridoxine hydrochloride.

22. The dual release oral dosage form of claim 1, wherein said immediate release composition comprises about 10 mg of doxylamine succinate and about 10 mg of pyridoxine hydrochloride, and said delayed release composition comprises about 10 mg of doxylamine succinate and about 10 mg of pyridoxine hydrochloride.

23. A method for alleviating the symptoms of nausea and vomiting in a mammal, said method comprising administering the dual release oral dosage form of claim 1 to a mammal in need thereof.

24. A method for alleviating the symptoms of nausea and vomiting of human pregnancy, said method comprising administering dual release oral dosage form of claim 1 to a pregnant human female in need thereof.

25. The method of claim 23, wherein said dual release oral dosage form is administered under fasted conditions.

26. The method of claim 24, wherein said dual release oral dosage form is administered under fasted conditions.

27. The method of claim 23, wherein said dual release oral dosage form is administered under fed conditions.

28. The method of claim 24, wherein said dual release oral dosage form is administered under fed conditions.

29. The method of claim 23, wherein said dual release oral dosage form is administered twice-a-day.

30. The method of claim 24, wherein said dual release oral dosage form is administered twice-a-day.

\* \* \* \* \*